US005837282A

United States Patent [19]
Fenske et al.

[11] Patent Number: 5,837,282
[45] Date of Patent: Nov. 17, 1998

[54] IONOPHORE-MEDIATED LIPOSOME LOADING

[75] Inventors: David B. Fenske, Surrey; Pieter R. Cullis, Vancouver; Kim Wong, Vancouver; Maurer Norbert, Vancouver; Johanna M. Leenhouts, Vancouver; Elisabeth Maurer, Vancouver; Nancy Boman, Surrey, all of Canada

[73] Assignee: University of British Columbia, Canada

[21] Appl. No.: 741,622

[22] Filed: Oct. 30, 1996

[51] Int. Cl.[6] .................................................... A61K 9/137
[52] U.S. Cl. ............................ 424/450; 264/4.1; 264/4.3
[58] Field of Search .............................. 424/450; 264/4.1, 264/4.3

[56] References Cited

U.S. PATENT DOCUMENTS

| | | | |
|---|---|---|---|
| 4,310,506 | 1/1982 | Baldeschwieler et al. | 424/1 |
| 4,560,665 | 12/1985 | Nakae et al. | 436/172 |
| 4,880,635 | 11/1989 | Janoff | 424/450 |
| 5,077,056 | 12/1991 | Bally et al. | 424/450 |
| 5,088,499 | 2/1992 | Unger et al. | |
| 5,169,637 | 12/1992 | Lenk et al. | |
| 5,192,549 | 3/1993 | Barenolz et al. | 424/450 |
| 5,316,771 | 5/1994 | Barenholz et al. | 424/450 |
| 5,352,435 | 10/1994 | Unger et al. | |
| 5,525,232 | 6/1996 | Veiro | 210/638 |
| 5,578,320 | 11/1996 | Janoff | 424/450 |
| 5,593,688 | 1/1997 | Balderschwieler | 424/450 |

FOREIGN PATENT DOCUMENTS

| | | |
|---|---|---|
| 96/26715 | 9/1996 | WIPO . |
| 96/32930 | 10/1996 | WIPO . |

OTHER PUBLICATIONS

Chonn et al., *Current Opinion in Biotechnology* 6:698–708 (1995).
Boman et al., *Liposomes in Biomedical Applications*, Shek, ed., Harwood Academic Publishers, Singapore, pp. 85–103 (1995).
Hope et al., *Liposomes in Biomedical Applications* Shek, ed., Harwood Academic Publishers, Singapore, pp. 121–134 (1995).
Mayer, et al., *Cancer Res.* 49:5922–5930 (1989).
Mayer, et al., *J. Liposome Res.* 1:463–480 (1990).
Boman, et al., *Biochim. Biophys. Acta* 1152:253–258 (1993).
Boman, et al., *Cancer Res.* 54:2830–2833 (1994).
Boman, et al., *J. Liposome Research*, 5:523–541 (1995).
Webb, et al., *Briti. J. Cancer*, 72:896–904 (1995).
Pressman, B.C., *Ann. Rev. Biochem.*, 45:501–530 (1976).
Veiro, J.A. and Cullis, P.R., A Novel for the Efficient Entrapment of $Ca^{2+}$ in Large Unilamellar Vesicles, *Biochim. Biophys. Acta* 1025, 109–115 (1990).
Chakrabarti, et al., Generation and Characterization of Iron and Barium Loaded Liposomes. *Biochim. Biophys. Acta* 1108, 233–239 (1992).

(List continued on next page.)

*Primary Examiner*—Gollamudi S. Kishore
*Attorney, Agent, or Firm*—Townsend and Townsend and Crew LLP

[57] ABSTRACT

Novel methods are provided for loading a weakly basic drug into liposomes utilizing an electoneutral transport system. In these methods, ionophores are utilized with liposomes having a metal ion gradient to facilitate the exchange of metal ions for protons. The transported metal ion will, in some embodiments, be complexed with a chelating agent which is present in the external media.

25 Claims, 11 Drawing Sheets

OTHER PUBLICATIONS

Wheeler et al., Ionophore–mediated Loading of $Ca^{2+}$ into Large Unilamellar Vesicles in Response to Transmembrane pH Gradients. *Molecular Membrane Biology,* 11, 151–157 (1994).

Madden et al., The Accumulation of Drugs with Large Unilamellar Vesicles Exhibiting a Proton Gradient: a survey. *Chem. Phys. Lipids* 53, 37–46 (1190).

Erdahl, et al., Effect of pH Conditions on $Ca^{2+}$ Transport Catalyzed by Ionophores A23187, 4–BrA23187, and Ionomycin Suggest Problems with Common Applications of these Compounds in Biological Systems. *Biophys. J.* 69, 2350–2363 (1995).

Waldeck, et al., $^{23}$Na–nuclear Magnetic resonance Study of Ionophore–mediated Cation Exchange Between Two populations of Vesicles, *Biophys. J.* 64, 1445–1455 (1993).

Kimmich et al., *Biochem J.,* 168 (1), pp. 81–99, (Oct. 5, 1977).

Vuilleumier P. et al., *Biochim Biophys Acta,* 467(1) pp. 12–19, (May 16, 1977).

Deamer et al., The Response of Fluorescent Amines to pH Gradients Across Liposome Membranes, *Biochim Biophys Acta,* 274, 323–335 (1972).

Erdahl, et al. *Biophys J.,* 66:1678–1693 (1994).

Leenhouts, et al., "New Procedures for the Loading of Doxorubicin Into Liposomes," *FASEB Journal,* vol. 11, No. 9, p. A1430 (1997).

CIPROFLOXACIN pK₁ = 6.0
pK₂ = 8.8

VINCRISTINE pK₁ = 5.0
pK₂ = 7.4

IONOPHORE-MEDIATED LIPOSOME LOADING

FIELD OF THE INVENTION

This invention relates to methods of preparing liposomes having encapsulated therapeutic agents. The liposomes may further having targeting moieties for the selective delivery of the therapeutic agent to a particular tissue.

BACKGROUND OF THE INVENTION

Liposomes, or lipid vesicles, are a recognized drug delivery system which can improve the therapeutic activity and increase the safety of a number of different pharmaceutical agents. To be useful in medical treatments, liposome formulations should have an efficient drug to lipid ratio, a practical shelf-life and be capable of reproducible preparation. High drug to lipid ratios reduce the non-therapeutic lipid "load" to the patient, and also lower the cost of manufacture, since less pharmaceutical is lost in the process of manufacture.

Liposomal carrier systems (vesicles) are microscopic spheres of one or more lipid bilayers arranged concentrically around an aqueous core. The vesicles have been shown to be suitable as carriers for both hydrophilic and hydrophobic therapeutic agents owing to their unique combination of lipophilic and hydrophilic portions. The structure of the lipid bilayer is similar to the membranes enveloping animal cells, and are a result of amphipathic lipids arranged such that the hydrophobic portions of the lipid orient toward the center of the bilayer while the hydrophilic headgroups orient towards the inner or outer aqueous phases.

Liposome formulations for pharmaceutical applications can be made either by combining drug and lipid before formation of the vesicles, or by "loading" lipid vesicles with drug after they are formed. Upon administration to a patient, liposomes biodistribute and interact with cells in the body according to route of administration, vesicular composition, and vesicular size. Charge, chemistry, and the inclusion on the vesicle surface of protective polymers or targeting moieties, all change the way liposomes behave in the patient.

Despite the earlier pioneering research in developing liposome formulations for pharmaceutical use, the further development of liposomes to administer pharmaceuticals has presented problems with regard to both drug encapsulation in the manufacturing process and drug release from the vesicle during therapy.

For drug encapsulation, there is a need to increase the trapping efficiency such that the drug to lipid ratio is as high as possible, while maintaining the original chemical integrity of both drug and lipid. Consequently, the drug loading process should be mild and not subject the lipids, liposomes or drugs to harsh conditions such as extreme pH, high temperatures, or both. Once administration to a patient has occurred, drug release is a factor. Rapid release of pharmaceuticals from liposomes reduce the biodistribution benefits sought in utilizing lipid vesicle carriers. Accordingly, efforts to optimize pharmaceutical loading and to reduce the rate of release of pharmaceuticals from lipid vesicles have continued. For clinical applications, the liposome formulations should be capable of existing stably in a formulated state or in a ready-to-mix kit to allow for shipping and storage.

The ability of transmembrane pH gradients ($\Delta$pH) to influence the drug loading of certain weak acids and weak bases has long been recognized. See, for example, Jacobs Quant. Biol. 8:30–39 (1940), Chapper, et al. in REGULATION OF METABOLIC PROCESSES IN MITOCHONDRIA Tager, et al. eds. Elsevier, Amsterdam, pp. 293–316 (1966), Crofts, J. Biol. Chem. 242:3352–3359 (1967), Crofts, REGULATORY FUNCTIONS OF BIOLOGICAL MEMBRANES, Jarnefelt, ed., Elsevier Publishing Co., Amsterdam, pp. 247–263 (1968), Rottenberg, Bioenergetics 7:61–74 (1975), and Rottenberg, Methods in Enzmol. 55:547–569 (1979). This behavior stems from the highly permeable nature of the neutral forms of these molecules, which contrasts with the impermeable nature of the charged forms. Thus, if a neutral amine (such as ammonia) diffuses across a biological membrane or vesicle exhibiting a $\Delta$pH (interior acidic), it will become protonated and therefore trapped in the vesicle interior. Recent work has involved the anticancer drugs doxorubicin and vincristine, which exhibit significantly reduced toxicity and equal or increased efficacy in liposomally-encapsulated formulations. See, for example, Mayer, et al., Cancer Res. 49:5922–5930 (1989), Mayer, et al., Cancer Letters 53:183–190 (1990), Mayer, et al., J. Liposome Res. 1:463–480 (1990), Harrigan, et al., Biochim. Biophys. Acta 1149:329–338 (1993), Boman, et al., Biochim. Biophys. Acta 1152:253–258 (1993), Boman, et al., Cancer Res. 54:2830–2833 (1994), and Boman, et al., J. Liposome Research 5:523–541 (1995). It has been recognized for some time that encapsulation of doxorubicin can decrease drug toxicity (particularly an acute cardiotoxicity), but until recently, most of the formulations involved passive entrapment methods, which suffered from low encapsulation levels and poor retention. The development of remote-loading methods, which involve addition of the drug to preformed LUVs exhibiting a $\Delta$pH, allowed increased trapping efficiencies to be achieved, producing significantly higher drug-to-lipid (D/L) ratios with improved retention. The basic remote-loading technique involves formation of the LUVs by extrusion in an acidic buffer (typically about pH 4.0), followed by formation of the pH gradient on a column of Sephadex G-50 equilibrated in a neutral buffer. This approach has led to formulations of both doxorubicin and vincristine which are now in clinical trials. See, Chonn, et al. Current Opinion in Biotechnology 6:698–708 (1995) and Boman, et al., LIPOSOMES IN BIOMEDICAL APPLICATIONS, Shek, ed., Harwood Academic Publishers, Singapore, pp. 85–103 (1995).

Unfortunately, not all drugs can be efficiently loaded using this method. The antibiotic ciprofloxacin, for example, has low solubility near neutral pH, which can lead to low entrapment values under certain conditions. See, Hope, et al., LIPOSOMES IN BIOMEDICAL APPLICATIONS, Shek, ed., Harwood Academic Publishers, Singapore, pp. 121–134 (1995).

In related work, others have shown that doxorubicin and the antibiotic ciprofloxacin can be loaded into LUVs exhibiting transmembrane gradients of ammonium sulfate. See, Lasic, et al., FEBS Lett. 312:255–258 (1992), Haran, et al., Biochim. Biophys. Acta 1151:201–215 (1993), and Lasic, et al., Biochim. Biophys. Acta 1239:145–156 (1995). Vesicles containing ammonium sulfate spontaneously form pH gradients when a quantity of neutral ammonia leaks out, leaving the associated protons within the vesicle interior. The uptake of drug, which causes a rise in internal pH, is coupled to the loss of more internal ammonia. Thus the ammonia gradient is a means of generating a pH gradient for drug uptake. The advantage of this technique lies in the gentler conditions used. As the vesicle interior is not buffered, the pH following drug uptake is higher than in the standard technique (see, Hope, et al. LIPOSOMES IN BIOMEDICAL APPLICATIONS (Shek, P.N., ed,), Harwood Academic Publishers, Singapore, pp. 121–134. (1995)), which could be an advantage for pH sensitive drugs and some lipids.

What is needed in the art are new methods for the preparation of stable liposome formulations of therapeutic agents which are easy to prepare, provide suitable retention of the therapeutic agent, and which provide high drug to lipid ratios. Quite surprisingly, the present invention fulfills these and other needs.

SUMMARY OF THE INVENTION

The present invention provides methods for loading a weakly basic drug into liposomes utilizing an electoneutral transport system.

In one aspect, the method of loading liposomes utilizes liposomes having an encapsulated medium comprising a salt of a divalent metal ion. Uptake of a weakly basic drug is accomplished by incubating these liposomes with an external solution comprising the drug and an ionophore which is capable of the electroneutral exchange across the liposome bilayer of one divalent metal ion for two protons. Preferably, the external medium containing the weakly basic drug will further comprise a chelating agent which coordinates any metal ion released to the external medium.

In another aspect of the invention, a method is provided in which liposomes having an encapsulated medium comprising a salt of a monovalent metal ion are incubated with an external solution comprising the weakly basic drug and an ionophore to form drug-loaded liposomes. In this aspect of the invention, the ionophore is present in the external medium in an initial amount of from about 0.1 ng to about 2000 ng per $\mu$mol of lipid.

In yet another aspect, the present invention provides compositions which are prepared by the above methods. In some preferred embodiments, the ionophore is removed from the compositions by gel exclusion chromatography or dialysis.

BRIEF DESCRIPTION OF THE DRAWINGS

In FIG. 6A, the external medium was 300 mM sucrose 3 mM EDTA (■) or 300 mM sucrose (●). The addition of A23187 (0.1 $\mu$g/$\mu$mol lipid) is indicated by the arrow. The uptake temperature was 60° C, and the initial D/L ratio was 0.35 (mol:mol).

In FIG. 9A, uptake experiments were performed for the following combinations of ionophore/internal salt: A23187/$MnSO_4$ (●), A23187/$MgSO_4$ (■), nigericin/$K_2SO_4$ (♦), and nigericin/$K_2$-tartrate (◇). The arrow indicates the addition of mouse serum (to a final concentration of 50%) and transfer of the sample to 37° C.

FIG. 10A illustrates the effect of spin columns on uptake of ciprofloxacin at 60° C. Uptake was monitored for LUVs containing 300 mM $K_2SO_4$ at a nigericin concentration of 1 ng/μmol lipid (■), and for LUVs which were preincubated with nigericin for 5 min at 60° C., and then passed down a spin column prior to addition of the drug (●).

DETAILED DESCRIPTION OF THE INVENTION

CONTENTS

Figure 1:
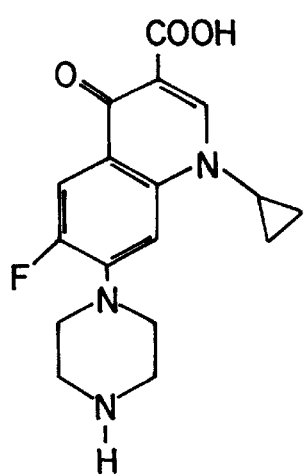
FIG. 1 shows the chemical structures of ciprofloxacin and vincristine and their associated pH values.
Figure 1:
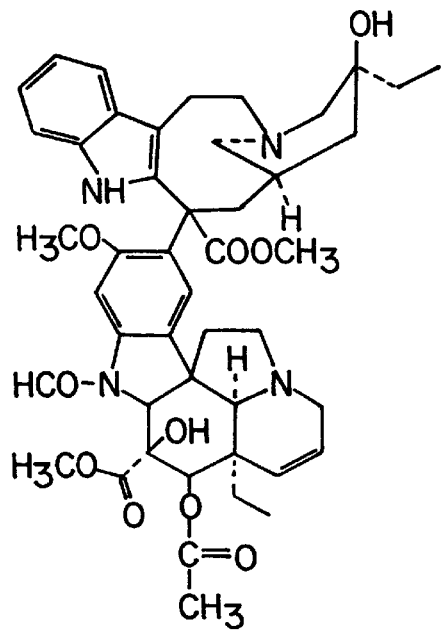

I. Glossary
II. General—Liposome Preparation
III. Ionophore-Mediated Loading
IV. Pharmaceutical Preparations
V. Administration of Liposomes
VI. Examples
VII. Conclusion I. Glossary Abbreviations and Definitions The following abbreviations are used herein: CHE, cholestrol hexadecyl ether; Chol, cholesterol; CIPRO, ciprofloxacin; EDTA, ethylenediamine tetraacetic acid; EGTA, ethylenebis(oxyethylenenitrilo)tetraacetic acid; D/L, drug-to-lipid ratio; DOX, doxorubicin; DSPC, distearoylphosphatidylcholine; LUVs, large unilamellar vesicles; NIG, nigericin; POPC, palmitoyl oleoyl phosphatidylcholine; SPM, sphingomyelin; RT, room temperature; TBE, Tris-Borate-EDTA (89 mM in Tris-borate and 2 mM in EDTA); HEPES, 4-(2-hydroxyethyl)-1-piperazineethanesulfonic acid; PBS, phosphate-buffered saline; VINC, vincristine.

As used herein, the term "ionophore" refers to a compound which forms a complex with a metal cation and assists the cation in crossing a lipid bilayer while further assisting the transport of H+ in the counter direction. Examples of suitable ionophores for the present invention include nigericin, monensin, dianemycin, A23187, 4-BrA23187, ionomycin and X-537A.

As used herein, the term "chelating agent" refers to a compound which forms a complex with a metal cation which does not cross a lipid bilayer. Examples of suitable chelating agents include EDTA, EGTA and QUIN-2.

As used herein, the term "weakly basic drug" refers to those therapeutic agents which contain a primary, secondary or tertiary amine function. Examples of weakly basic drugs include ciprofloxacin, mitoxantrone, epirubicin, daunorubicin, doxorubicin, vincristine, vinblastine, lidocaine, chlorpromazine, dibucaine, propranolol, timolol, quinidine, pilocarpine, physostigmine, dopamine, serotonin, imipramine, diphenhydramine, quinine, chloroquine, quinacrine and codeine.

The term "lipid" refers to any suitable material resulting in a bilayer such that the hydrophobic portion of the lipid material orients toward the bilayer interior while the hydrophilic portion orients toward the aqueous phase. Amphipathic lipids are necessary as the primary lipid vesicle structural element. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group (s). The preferred amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid and glycosphingolipid families are also within the group designated as lipid. Additionally, the amphipathic lipids described above may be mixed with other lipids including triacyglycerols and sterols.

II. General—Liposome Preparation

The liposomes which are used in the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Other suitable lipids include phosphonolipids in which the fatty acids are linked to glycerol via ether linkages rather than ester linkages. Liposomes useful in the present invention may also be composed of sphingomyelin or phospholipids with head groups other than choline, such as ethanolamine, serine, glycerol and inositol. Preferred liposomes will include a sterol, preferably cholesterol, at molar ratios of from 0.1 to 1.0 (cholesterol:phospholipid). Most preferred liposome compositions are distearoylphosphatidylcholine/cholesterol, dipalmitoylphosphatidylcholine/cholesterol, and sphingomyelin/cholesterol. Methods used in sizing and filter-sterilizing liposomes are discussed below.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes,* Marc J. Ostro, ed., Marcel Dekker, Inc., New York, 1983, Chapter 1, and Hope, et al., *Chem. Phys. Lip.* 40:89 (1986), all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in a suitable solvent, such as tertiary butanol, and then lyophilized to form a more homogeneous lipid mixture which is in a more easily hydrated powder-like form. This film or powder is covered with an aqueous buffered solution of a monovalent or divalent metal ion and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.15 microns are preferred.

As noted above, the present invention provides a method for loading drugs into liposomes using an electroneutral transport system. In this method, liposomes are first produced having different encapsulated and external media. More specifically, liposomes are prepared which encapsulate a solution of a monovalent or divalent metal ion. For a typical liposome preparation technique (see discussion above), this solution will surround the liposomes as they are formed, and thus the liposomes' original external medium will have the same composition as the encapsulated solution. The replacement of the external solution can be accomplished by various techniques, such as, by passing the liposome preparation through a gel filtration column which has been equilibrated with a second aqueous buffered solution, or by centrifugation, dialysis, or related techniques.

Once liposomes having suitable internal and external media have been prepared, the process of loading the drug into the liposomes reduces to the step of incubating the liposomes with the drug and an ionophore capable of transporting the encapsulated metal ion across the liposome bilayer.

III. Ionophore-Mediated Loading

Figure 2:
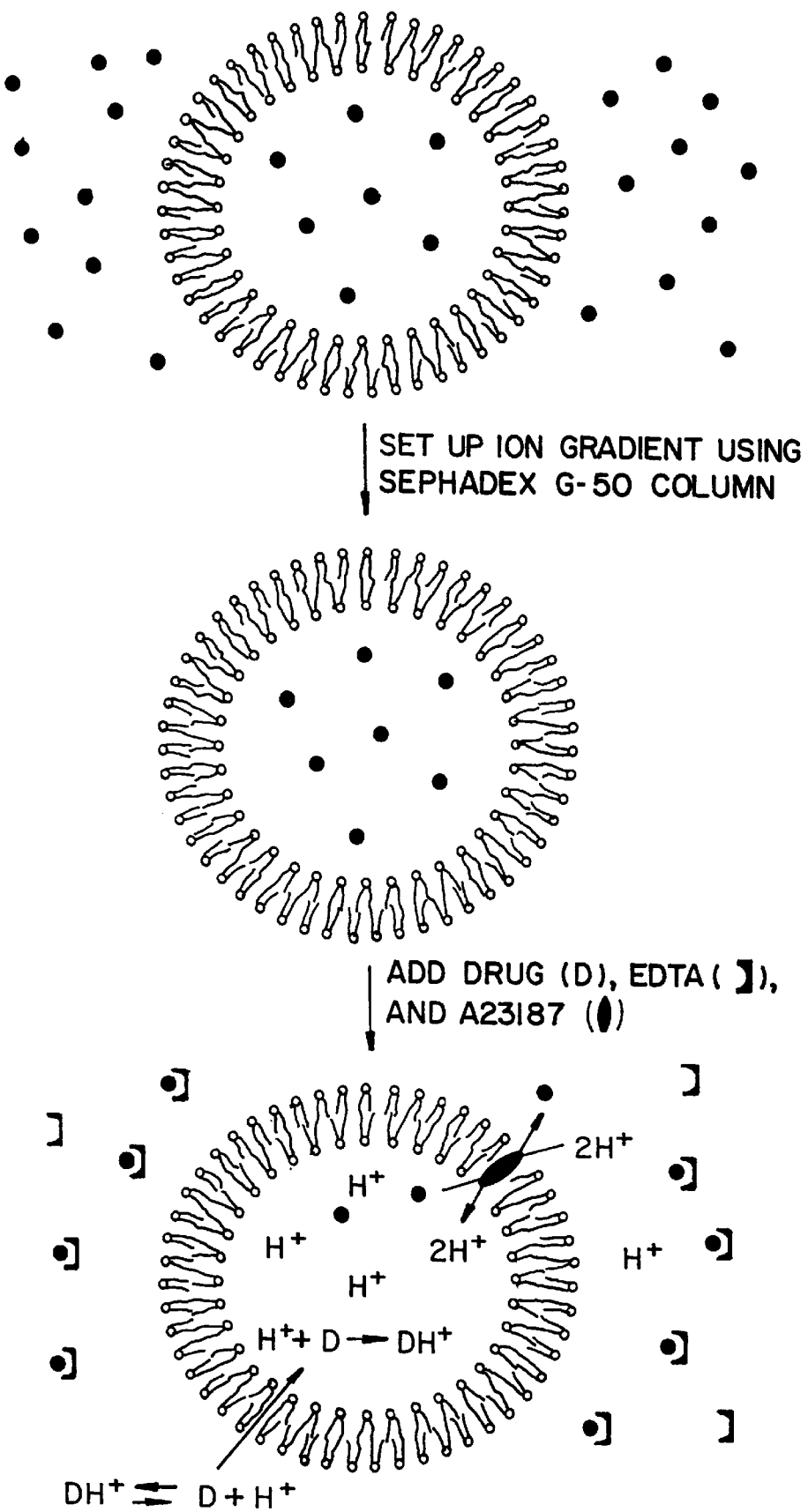
FIG. 2 provides a representation of ionophore-dependent loading of therapeutic agents into liposomes for the $Mn^{++}$/A23187 system. The filled circles represent $Mn^{2+}$ ions.

The general principles behind ionophore-dependent drug uptake are illustrated in FIG. 2. Large unilamellar vesicles (LUVs) are formed which entrap a high concentration of a metal ion such as $K^+$ or $Mn^{2+}$, and an ion gradient is established by removal of the external metal ion (FIG. 2, top and center). A drug is added to the external medium, and uptake is initiated by addition of an ionophore which couples the outward transport of the metal ion to the inward movement of $H^+$. This creates a transient pH gradient (inside acidic) which results in uptake of compounds with weak base characteristics, such as the drugs ciprofloxacin (CIPRO) and vincristine (VINC). The ionophore nigericin facilitates a one-for-one exchange of $K^+$ for $H^+$, while A23187 transports two $H^+$ for every $M^{2+}$ (where M=Ca, Mn, Mg, Fe or Ba). Both processes are electroneutral.

Although the general principle is straightforward, a number of parameters can be varied in order to achieve optimal drug uptake. These include lipid composition, internal salt concentration, the ionophore to lipid ratio, and the pH of the internal and external solutions. In addition, systems utilizing divalent cations can be further improved by the addition of an external chelator to drive uptake by reducing the effective concentration of the metal ion in the external solution (FIG. 2, bottom).

(a) Drug Loading

In one aspect, the present invention provides methods of loading weakly basic drugs into liposomes comprising incubating liposomes having an encapsulated medium comprising a salt of a divalent metal ion with an external solution comprising the weakly basic drug and an ionophore to form drug-loaded liposomes.

As already discussed, the liposomes used in the present invention can be any of a variety of lipid vesicles including, for example, large unilamellar vesicles (LUVs), medium or small unilamellar vesicles (MUVs and SUVs, respectively), and multilamellar vesicles (MLVs). Preferably, the liposomes are LUVs. The liposomes are formed or, in some cases, rehydrated using a solution of a divalent metal ion which is present as a salt.

While the concept of drug loading using divalent metal ions can be applied to almost any divalent metal ions, those which are particularly suitable for this aspect of the invention include $Mn^{+2}$, $Mg^{+2}$ and $Ca^{+2}$. Additionally, the salts of the divalent metal ion can be any of a variety of salts. Preferably, the salts are pharmaceutically acceptable salts which are soluble in aqueous media or which are soluble in aqueous media containing a portion of a solubilizing organic solvent such as THF or DMF. Examples of suitable salts are chlorides, sulfates, acetates, tartrates, citrates and phosphates. Preferably, the salts used are sulfate salts. The concentration of the divalent metal ion salts present in the encapsulated medium of the liposomes will also affect the rate and extent of drug loading. Typically, the divalent metal ions will be present in an amount of from about 50 mM to about 1M, preferably from about 100 mM to about 800 mM, and more preferably from about 250 mM to about 650 mM.

Once the liposomes are formed having an encapsulated medium containing the divalent metal ions, a gradient is established across the lipid bilayer. Establishment of the gradient can be carried out by replacing the external medium with a medium substantially lacking the divalent metal ion, or by diluting the external medium to reduce the concentration of divalent metal ion, or by dialysis. In any case, the object is to establish a gradient across the lipid bilayer in which greater concentrations of metal ion are present in the interior of the vesicles than in the external medium.

After the metal ion gradient has been established (or coincident with the establishment of the gradient), a weakly basic drug is added to the external medium. The weakly basic drug can be any of a variety of therapeutic or diagnostic agents which possess a primary, secondary or tertiary amine functional group. Examples of suitable weakly basic drugs are ciprofloxacin, mitoxantrone, epirubicin, daunorubicin, doxorubicin, vincristine, vinblastine, lidocaine, chlorpromazine, dibucaine, propranolol, timolol, quinidine, pilocarpine, physostigmine, dopamine, serotonin, imipramine, diphenhydramine, quinine, chloroquine, quinacrine and codeine. One of skill in the art will appreciate that other weakly basic drugs can be loaded into liposomes will equal effectiveness. Moreover, the present methods can be applied to the loading of weakly basic diagnostic agents as well.

Loading of the drug into the liposome is initiated upon introduction of a suitable ionophore into the external medium. Ionophores which are useful in the present invention are those which facilitate the electroneutral transport of a metal ion out of the lipid vesicle in exchange for inward movement of hydrogen ions. Examples of ionphores which are useful for divalent metal ions include A23187, ionomycin and X-537A. The ionophore X-537A (Lasalocid) is available from Aldrich Chemical Co. (Milwaukee, Wis., U.S.A.) or can be isolated or prepared by methods described in U.S. Pat. No. 3,715,372, the disclosure of which is incorporated herein by reference. The ionophore A23187 is available from Sigma Chemical Co. The amount of the ionophore which is used will typically depend on the nature and type of liposome composition and will be from about 10 ng per $\mu$mol of lipid to about 2000 ng per $\mu$mol of lipid. Preferably, the amount of ionophore will be about 100 to about 500 ng per $\mu$mol of lipid.

As noted, the drug is loaded into the liposomes in response to a transient pH gradient which is established as a result of the electroneutral exchange of metal ions for hydrogen ion facilitated by the ionophore. This loading process will occur at ambient temperatures, but can also be conducted at elevated temperatures of, for example, 40° C. to about 75° C., preferably from about 50° C. to about 65° C.

In one group of embodiments, the external solution will further comprise a chelating agent, which serves to prevent the divalent metal ion from migrating back into the liposome. Suitable chelating agents include, for example, EDTA, EGTA and QUIN-2. Preferably, the amount of chelating agent which is present in the external solution will be from about 0.5 mM to about 300 mM, more preferably from about 1.0 mM to about 50 mM.

The present invention provides additional methods of loading a weakly basic drug into liposomes. In these methods, liposomes having an encapsulated medium comprising a salt of a monovalent metal ion are incubated in an external solution comprising the weakly basic drug and an ionophore. The ionophores which are useful in these methods are also electroneutral but are specific for monovalent metal ions and are present in amounts of from about 0.1 ng to about 2000 ng per $\mu$mol of lipid, preferably from about 0.1 ng to about 100 ng per $\mu$mol of lipid, and more preferably from about 0.5 ng to about 5.0 ng per $\mu$mol of lipid. Examples of ionophores which are specific for monovalent metal ions include nigericin, monensin, dianemycin. Other features and preferred conditions for this aspect of the invention are generally as described above for the methods involving divalent metal ions.

Once the drug has been loaded into the liposomes, by either the monovalent or divalent methods, the compositions can be used directly, or the composition can be further treated to remove any unloaded drug as well as the ionophore. A number of methods are available for the removal of ionophore from the liposome compositions including, for example, gel exclusion chromatography, dialysis, or treatment with biobeads. Preferably, the ionophore is removed from the liposome compositions using gel exclusion chromatography.

IV. Pharmaceutical Preparations

The liposome compositions prepared by the methods described above can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt containing carriers, the carrier is preferably added following liposome formation. Thus, after the liposome is formed and loaded with a suitable drug, the liposome can be diluted into pharmaceutically acceptable carriers such as normal saline. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents which protect lipids against free-radical and lipid-peroxidative damages on storage. Lipophilic free-radical quenchers, such as $\alpha$-tocopherol and water-soluble iron-specific chelators, such as ferrioxamine, are suitable.

The concentration of liposomes in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration. The amount of liposomes administered will depend upon the particular drug used, the disease state being treated and the judgement of the clinician but will generally be between about 0.01 and about 50 mg per kilogram of body weight, preferably between about 0.1 and about 5 mg/kg of body weight.

It is often desirable to include polyethylene glycol (PEG)-modified phospholipids, PEG-ceramide, or ganglioside $G_{M1}$-modified lipids to the liposomes. Addition of such components prevents liposome aggregation and provides a means for increasing circulation lifetime and increasing the delivery of the loaded liposomes to the target tissues. Typically, the concentration of the PEG-modified phospholipids, PEG-ceramide or $G_{M1}$-modified lipids in the liposome will be about 1–15%.

Overall liposome charge is also an important determinant in liposome clearance from the blood. Charged liposomes are typically taken up more rapidly by the reticuloendothelial system (Juliano, *Biochem. Biophys. Res. Commun.* 63:651 (1975)) and thus have shorter half-lives in the bloodstream. Liposomes with prolonged circulation half-lives are typically desirable for therapeutic and certain diagnostic uses. For instance, liposomes which can be maintained from 8, 12, or up to 24 hours in the bloodstream are particularly preferred.

In another example of their use, drug-loaded liposomes can be incorporated into a broad range of topical dosage forms including but not limited to gels, oils, emulsions and the like. For instance, the suspension containing the drug-loaded liposomes can be formulated and administered as topical creams, pastes, ointments, gels, lotions and the like.

The present invention also provides liposome compositions in kit form. The kit will typically be comprised of a container which is compartmentalized for holding the various elements of the kit. The kit will contain the compositions of the present inventions, preferably in dehydrated form, with instructions for their rehydration and administration. In still other embodiments, the drug-loaded liposomes will have a targeting moiety attached to the surface of the liposome. Methods of attaching targeting moieties (e.g., antibodies, proteins) to lipids (such as those used in the present particles) are known to those of skill in the art.

Dosage for the drug-loaded liposome formulations will depend on the ratio of drug to lipid and the administrating physician's opinion based on age, weight, and condition of the patient.

V. Administration of Liposomes

Once the therapeutic agent has been "loaded" into the liposomes, the combination can be administered to a patient by a variety of techniques.

Preferably, the pharmaceutical compositions are administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Raham et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Particular formulations which are suitable for this use are found in *Remington's Pharmaceutical Sciences,* Mack Publishing Company, Philadelphia, Pa., 17th ed. (1985). Typically, the formulations will comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Dosage for the liposome formulations will depend on the ratio of drug to lipid and the administrating physician's opinion based on age, weight, and condition of the patient.

The methods of the present invention may be practiced in a variety of hosts. Preferred hosts include mammalian species, such as humans, non-human primates, dogs, cats, cattle, horses, sheep, and the like.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The compositions of the present invention which further comprise a targeting antibody on the surface of the liposome are particularly useful for the treatment of certain malignant diseases, such as ovarian adenocarcinoma that has metastasized throughout the peritoneal cavity and metastatic lesions to the subarachnoid space that commonly adhere to the arachnoid or pia mater and threaten compression of the spinal cord. Adenocarcinoma of the breast commonly exhibits such a metastatic pattern.

VI. Examples

In the examples below, Examples 1–4 illustrate the ionophore-mediated uptake of ciprofloxacin and vincristine into preformed liposomes. Example 5 illustrates the stability of the liposomal compositions. Example 6 illustrates the removal of ionophore from the drug-loaded compositions and Example 7 provides some pharmacokinetic data.

Materials

DSPC was obtained from Northern Lipids, Inc. (Vancouver, B.C., Canada). Egg SPM, cholesterol, nigericin, and A23187 were obtained from Sigma Chemical Co. (St. Louis, Mo., U.S.A.). Vincristine sulfate was obtained from Eli Lilly Canada Inc. (Scarborough, Ontario, Canada) or from Pharmacia, Inc. (Kalamazoo, Mich., U.S.A.) and [$^3$H] vincristine from Amersham (Oakville, Ontario, Canada). Ciprofloxacin and [$^{14}$C]ciprofloxaxin were generous gifts from Bayer (Etobioke, Ontario, Canada). [$^3$H]CHE and [$^{14}$C]CHE were obtained from Dupont New England Nuclear (Boston, Mass., U.S.A.). Normal mouse serum was obtained from Cedar Lane Laboratories (S. San Francisco, Calif., U.S.A.). All other chemicals used in these Examples were of reagent grade and all solvents used were HPLC grade.

Methods

Preparation of Lipid Vesicles

DSPC/Chol and SPM/Chol (55:45 mol:mol) lipid mixtures, containing a trace of either [$^{14}$C]CHE or [$^3$H]CHE, were prepared by lyophilization from t-butanol. The lipid film was hydrated in the salt of choice and subjected to 5 cycles of freeze-thawing using liquid nitrogen and water at 60° C., with vigorous vortexing of the lipid between each thaw and freeze cycle. LUVs were prepared by extruding the lipid emulsion through polycarbonate filters with a 0.1 μm pore size under high pressure (300–400 psi) at 60° C. (Hope, et al., *Biochim. Biophys. Acta* 812:55–65 (1985)). Lipids were hydrated with a variety of salt solutions, including $K_2SO_4$, $KH_2PO_4$, $K_2HPO_4$, $K_2$-tartrate, $CaCl_2$, $MnSO_4$, and $MgSO_4$. The salt concentrations were 300 mM or (in a few cases) 600 mM; for some experiments the pH was adjusted, usually in the range of 6–7.5.

Formation of Metal Cation Gradient

LUVs exhibiting a transmembrane salt gradient were prepared by solvent exchange using columns of Sephadex G-50 (1.5×10 cm) pre-equilibrated with 300 mM sucrose (often buffered). Salt gradients were also established by gel filtration chromatography using spin columns (Pick, *Arch. Biochem. Biophys.* 212:186–194 (1981)) in which the equilibrated G-50 gel is packed into a 1 mL disposable syringe by centrifugation to 760×g. To establish the gradient, 50–100 μL aliquots of the LUVs are applied to each spin column and centrifuged at 760×g on a desktop centrifuge for 2 minutes. In a few cases, the gradient was formed by dialysis.

Drug leakage in response to mouse serum

In order to model the potential release of drug from LUVs in vivo, an in vitro assay was used to give a qualitative comparison of the leakage of different drugs from the ionophore systems. In this assay, equal volumes of the liposomal drug formulation and of mouse serum are combined in a test tube and incubated at 37° C. Leakage of the drug from the LUVs is assayed by removal of aliquots for spin column analysis.

Drug and Lipid Assays

Ciprofloxacin concentrations were determined by measuring the absorbance at 275 am following disruption of the vesicles and solubilization of the drug by a Bligh and Dyer extraction procedure. See, Hope, et al., LIPOSOMES IN BIOMEDICAL APPLICATIONS, Shek, ed., Harwood Academic Publishers, Singapore, pp. 121–134 (1995). Vincristine concentrations were determined by measuring the absorbance in 80% ethanol at 295 nm (Madden, et al., *Chem. Phys. Lipids,* 53:37–46 (1990)). [$^{14}$C]CIPRO was diluted with cold CIPRO and the specific activity was determined by liquid scintillation counting and absorbance spectroscopy. The specific activity of [$^{3}$H]VINC was determined in the same manner. For experiments involving [$^{14}$C]CIPRO, the lipid mixtures were labeled using trace amounts of [$^{3}$H]CHE. For [$^{3}$H]VINC uptake the lipid was labeled with [$^{14}$C]CHE. Lipid specific activities were determined by liquid scintillation counting and by quantification of phospholipid via phosphate assays. See, Fiske, et al., *J. Biol. Chem.,* 66:375–400 (1925). For all uptake experiments, D/L ratios were determined by dual label liquid scintillation counting. These were compared with D/L ratios obtained by chemical and spectrophotometric assays and found to be identical.

Fluorimetric assay for A23187

The quantity of A23187 in SPM/Chol LUVs was determined by measuring the fluorescence intensity of the ionophore at an emission wavelength of 437 nm following solubilization of the liposomal formulation and complexation of the released divalent cations. Briefly, an aliquot of LUV/A23187 (corresponding to 5 μmol total lipid) was combined with a 333 mM EDTA solution (3 μL) and the volume was made up to 1 mL with ethanol:methanol (70:30 v:v). The sample was vortexed until clear, and the fluorescence intensity was measured. Calibration standards were prepared by the addition of known aliquots of A23187 to a 1 mL solution consisting of ethanol:methanol (70:30 v:v) and containing 5 mM total lipid.

In vivo pharmacokinetics

SPM/Chol vesicles (100 nm) were used (55:45; mole %). The vesicles were prepared in a 300 mM $K_2SO_4$ solution or 300 mM $MnSO_4$ and the external medium was exchanged with 300 mM sucrose, 20 mM HEPES, pH 7.0 by overnight dialysis. Ciprofloxacin was loaded at a drug-to-lipid ratio of 0.2 (mol:mol). Vincristine was loaded at a D/L ratio of 0.05:1 (wt:wt). Uptake of the drug was accomplished in the following manner: to an aliquot of liposomes was added either nigericin (1 ng per μmol of lipid) or A23187 (0.1 μg/μmol lipid) along with an appropriate amount of drug. For the A23187 experiments, EDTA was present in the external medium at 30 mM. The resulting solution was heated at 65° C. for 30 min for ciprofloxacin or for 15 min for vincristine.

Each sample was diluted with 300 mM sucrose to allow for a drug dose in mice of 15 mg/kg for ciprofloxacin or 2 mg/kg for vincristine. Each mouse was injected via a lateral tail vein with 200 μL total volume. ICR mice were used for ciprofloxacin studies and BDF1 mice were used for the vincristine studies. At varying time points, mice were anaesthetized and blood was collected via cardiac puncture. Blood was immediately centrifuged at 500 g and plasma was collected for lipid and drug determination.

EXAMPLE 1

This example illustrates the uptake of ciprofloxacin in response to a potassium ion gradient in the presence of the ionophore nigericin.

Liposomes were prepared as described in the general methods above. Uptake of ciprofloxacin was performed at 60° C. at a total lipid concentration of 5 mM (1 mL volume). The initial D/L ratio was either 0.2 or 0.3 (mol:mol). The LUVs and drug were combined and incubated for a period of 15 min at 60° C. An aliquot (100 μL) was removed in order to determine the initial D/L ratio, and a further aliquot (50–100 μL) was passed down a spin column to assess any uptake prior to the addition of the ionophore. Nigericin (in ethanol, about 5 μL) was added to the suspension to provide the desired concentration (from <1.0 ng/μmol lipid to 1.0 μg/μmol lipid). Aliquots were removed and applied to spin columns to monitor uptake of the drug over time.

Figure 3A:
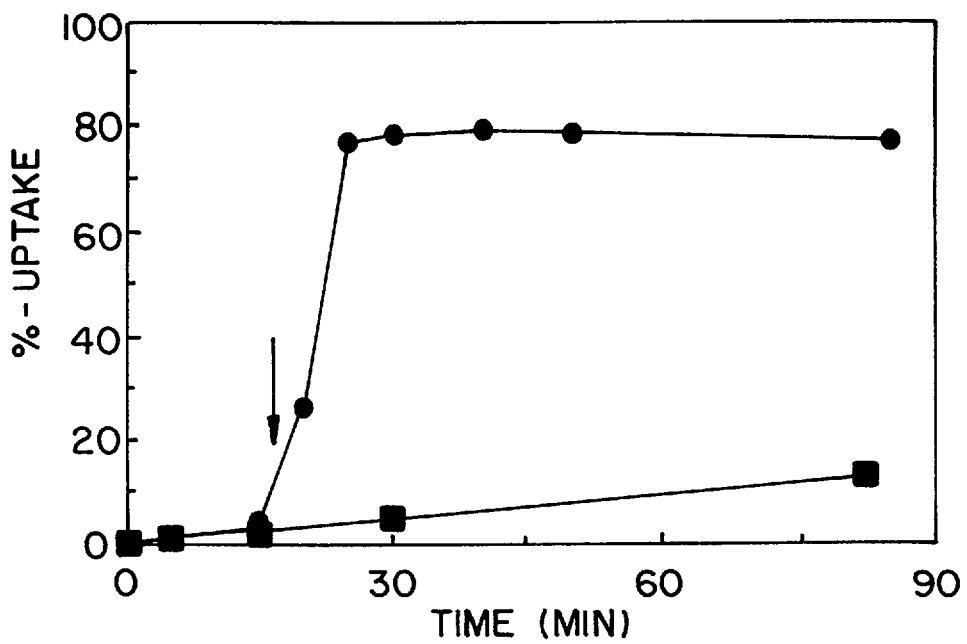
FIGS. 3A and B illustrate the effect of nigericin concentration on the uptake of ciprofloxacin in 100 nm DSPC/Chol LUVs containing 300 mM $K_2SO_4$ (FIG. 3A). The nigericin was present at 1 $\mu$g/$\mu$mol lipid (●) or at 0.01 ng/$\mu$mol lipid (■). No uptake of drug occurred prior to the addition of nigericin, which is indicated by the arrow. The initial D/L ratio was 0.3, and the uptake temperature was 60 ° C.
Figure 3B:
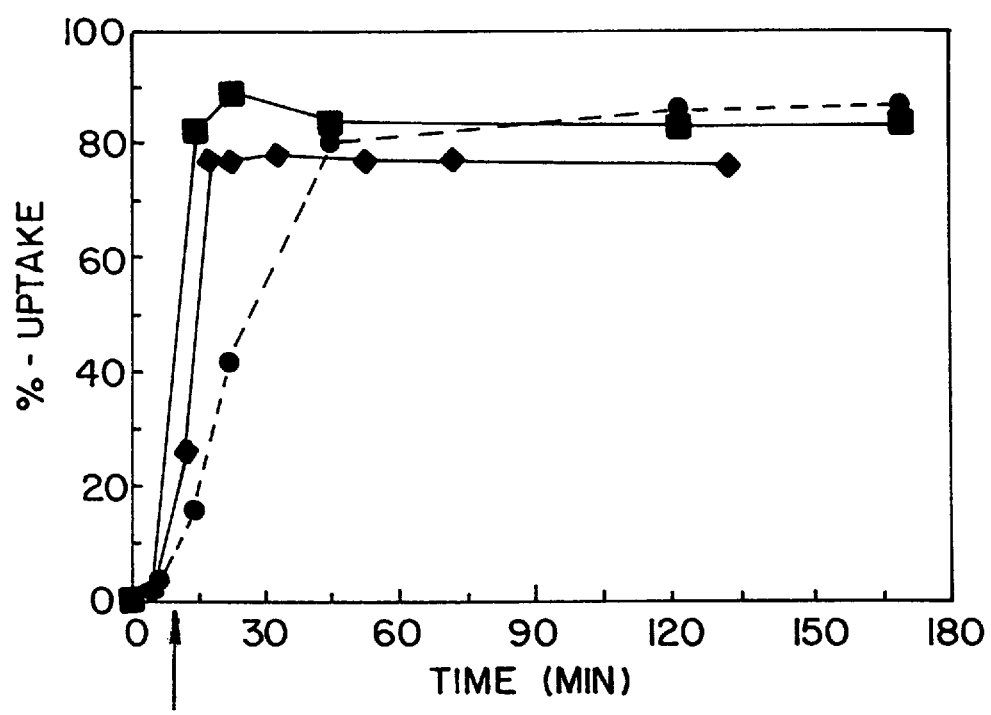
FIG. 3B illustrates the effect of nigericin concentration on the uptake of ciprofloxacin in 100 nm DSPC/Chol LUVs containing 600 mM $K_2SO_4$. The nigericin was present at 0.1 $\mu$g/$\mu$mol lipid (♦), at 1 $\mu$g/$\mu$mol lipid (■), or at 0.1 $\mu$g/$\mu$mol lipid (●; dotted line). No uptake of drug occurred prior to the addition of nigericin, which is indicated by the arrow. The initial D/L ratio was 0.3–0.37, and the uptake temperature was 60 ° C.

The uptake of CIPRO in 100 nm DSPC/Chol (55:45) LUVs containing 300 mM $K_2SO_4$ is illustrated in FIG. 3A. The external solvent was 300 mM sucrose (no pH adjustment). Little or no drug uptake occurred in response to the $K^+$ gradient alone, whereas within 5 minutes of addition of nigericin (indicated by the arrow) at a concentration of 1 μg/μmol lipid, 80% uptake was observed. The process was extremely rapid, giving high entrapment levels within minutes, with excellent retention observed over 3 hours at 60° C. The observed uptake was not influenced by increasing the internal salt concentration to 600 mM (FIG. 3B).

The rapid uptake observed in FIG. 3A suggested that the ionophore levels were higher than necessary. Consequently, the effect of reducing NIG levels was examined at 300 mM and 600 mM $K_2SO_4$. When the levels were reduced by a factor of $10^5$ (from 1 μg NIG/μmol lipid to 0.01 ng NIG/μmol lipid), only 12% uptake was observed after 80 minutes (FIG. 3A). For LUVs containing 600 mM $K_2SO_4$, no change in uptake was observed by reducing the ionophore by a factor of 10 (to 0.1 μg NIG/μmol lipid) or even by a factor of $10^3$ (to 1 ng NIG/μmol lipid) (FIG. 3B). However, a $10^4$-fold reduction resulted in a significant decrease in the rate of uptake of CIPRO (FIG. 3B), with at least 45 min required to obtain uptake levels of 80% or greater. Thus a NIG concentration of about 1 ng/μmol lipid was found to be ideal in order to obtain optimal loading levels within a reasonable time span. Under appropriate conditions (see below) this can be reduced to 0.5 ng NIG/μmol lipid.

The initial experiments described above were performed using DSPC/Chol LUVs, a composition giving rise to highly ordered (and therefore relatively impermeable), stable vesicles. These vesicles have also been utilized in formulations of VINC and DOX (see, Mayer, et al. *Cancer Res.* 49:5922–5930 (1989); Mayer, et al. *J. Liposome Res.* 1:463–480 (1990); Boman, et al., *Biochim. Biophys. Acta* 1152:253–258 (1993); and Boman, et al. *Cancer Res.* 54:2830–2833 (1994)). Recently, an excellent VINC formulation was achieved using SPM/Chol (55:45) LUVs in conjunction with the standard pH gradient remote-loading technique (see, Boman, et al., *J. Liposome Research* 5:523–541 (1995)) and Webb, et al., *Brit. J. Cancer* 72:896–904 (1995)). In order to examine whether acceptable uptake can be achieved with a SPM/Chol composition using an ionophore method, the uptake of CIPRO (and VINC) in 100 nm SPM/Chol LUVs using both nigericin and A23187 (below) was examined. As the primary motivation was to achieve a formulation with pharmacological potential, it was important to obtain uptake levels as close to 100% as possible. Therefore the initial D/L ratio was reduced from 0.3 to 0.2.

For 100 nm SPM/Chol LUVs containing 300 mM $K_2SO_4$ pH 7.4, in an external medium of 300 mM sucrose, only 60% uptake of CIPRO was observed at 60° C. for an initial D/L=0.2 at I ng NIG/μmol lipid (Table 1). This was improved to 80% by the use of HEPES-buffered sucrose (20 mM HEPES in 300 mM sucrose, pH 7.0) as the external medium, with a further marginal increase (85–90% uptake) observed when the internal pH was lowered to pH 6.1 (Table 1). Thus, the SPM-containing vesicles display similar %-uptake values to the DSPC-containing vesicles.

Figure 4:
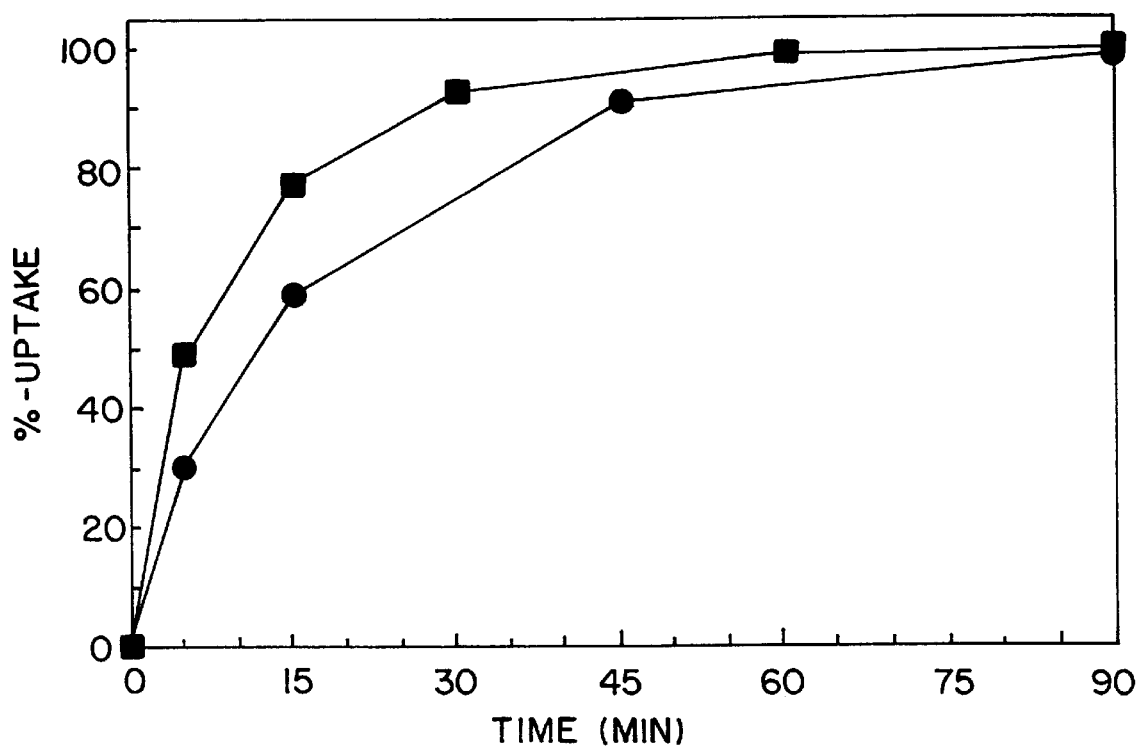
FIG. 4 illustrates the effect of external pH on the uptake of ciprofloxacin in 100 nm SPM/Chol LUVs containing 300 mM $K_2SO_4$. For the uptake at 60° C., the nigericin was present at 1 ng/$\mu$mol lipid, and the external medium was 300 mM sucrose 15 mM EDTA pH 6.2 (■). For the uptake at 70° C., the nigericin was present at 0.5 ng/$\mu$mol lipid, and the external medium was 300 mM sucrose 15 mM EDTA pH 5.5 (●). The nigericin was added at time 0. The initial D/L ratio was 0.2.

Significant improvement in CIPRO uptake was also observed by lowering the external pH, as shown in FIG. 4. When HEPES-buffered sucrose pH 6.2 was present in the external medium, 100% uptake was achieved after 60 minutes at 60° C. (for 1 ng NIG/μmol lipid). The same result was obtained at 70° C. when the ionophore concentration was reduced to 0.5 ng NIG/μmol lipid (for an external pH of 5.5), although 90 minutes were required to achieve 100% uptake (FIG. 4). A summary of these results is given in Table 1.

EXAMPLE 2

This example illustrates the nigericin-mediated uptake of vincristine into SPM/Chol or DSPC/Chol liposomes containing potassium ion gradients.

Figure 5:
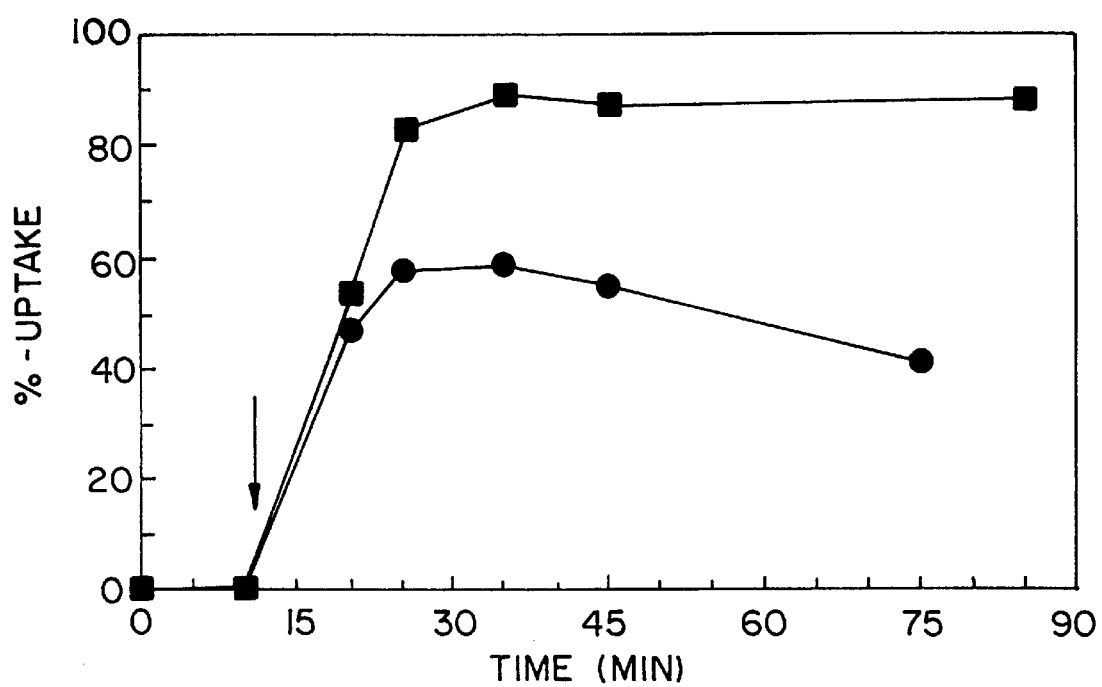
FIG. 5 illustrates the effect of external pH on the uptake of vincristine in 100 nm SPM/Chol LUVs containing 300 mM $K_2SO_4$. The external medium was 300 mM sucrose (approximate pH=6) (■) or 20 mM HEPES 300 mM sucrose pH 7.5 (●). The nigericin was added at t=12 min and was present at 1 ng/$\mu$mol lipid. The uptake temperature was 60° C., and the initial D/L ratio was 0.05 (wt:wt).

The uptake of VINC into SPM/Chol LUVs containing 300 mM $K_2SO_4$ was carried out at 60° C. as described above for ciprofloxacin. The results are shown in FIG. 5. As with CIPRO, no uptake was observed prior to the addition of nigericin (arrow). In the presence of external HEPES-buffered sucrose pH 7.5, the uptake was low (only 60%), with poor retention over 75 minutes. This was greatly improved when the external solvent was 300 mM sucrose, giving nearly 90% encapsulation and excellent retention. A further improvement was obtained (93–95%) for LUVs prepared in 300 mM $K_2SO_4$ pH 7.4 with an external pH of 6 (either 20 mM HEPES 300 mM sucrose or 20 mM MES 300 mM sucrose) (see FIG. 9B).

Reasonable encapsulation of VINC (80%) was also observed for 100 nm SPM/Chol LUVs containing 300 mM $KH_2PO_4$, but not for LUVs prepared in 300 mM $K_2HPO_4$ (<5%) (Table 2). In the latter case, the nigericin-dependent inward movement of protons is expected to form a phosphate buffer (near pH 7), which apparently prevents formation of a pH gradient.

Uptake of VINC in response to transmembrane gradients of $K_2$-tartrate has also been investigated in DSPC/Chol LUVs (Table 2). Uptake values of 85–90% were obtained within 15 min at 60° C. using 300 mM $K_2$-tartrate pH 7.4 as the internal salt, and HEPES-buffered sucrose pH 5.3–6.3 as the external medium. The ionophore concentration was 1 ng

TABLE 1

Summary of Ciprofloxacin Loading Using Nigericin/$K^+$ Systems

| Lipid Composition | Internal Salt[a] | $D/L_i$[b] | $I/L$[c] | %-uptake | Retention | T (°C.) | external solution: 300 mM sucrose + |
|---|---|---|---|---|---|---|---|
| (A) Ciprofloxacin | | | | | | | |
| DSPC/Chol | $K_2SO_4$ | 0.3 | 1000 | 80 | excellent | 60 | |
| DSPC/Chol | 600 mM $K_2SO_4$ | 0.3 | 100 | 80 | excellent | 60 | |
| DSPC/Chol | 600 mM $K_2SO_4$ | 0.3 | 1 | 80 | excellent | 60 | |
| DSPC/Chol | $K_2SO_4$ | 0.3 | 0.01 | 12 | n.a. | 60 | |
| DSPC/Chol | 600 mM $K_2SO_4$ | 0.37 | 0.1 | 85 | excellent | 60 | |
| SPM/Chol | $K_2SO_4$ pH 7.4 | 0.2 | 1 | 80 | excellent | 60 | 20 mM Hepes pH 7.0 |
| SPM/Chol | $K_2SO_4$ pH 7.4 | 0.2 | 1 | 75 | excellent | 60 | 20 mM Hepes pH 6.0 |
| SPM/Chol | $K_2SO_4$ pH 7.4 | 0.2 | 1 | 60 | fair | 60 | |
| SPM/Chol | $K_2SO_4$ pH 6.1 | 0.2 | 1 | 90 | excellent | 60 | 20 mM Hepes pH 7.0 |
| SPM/Chol | $K_2SO_4$ pH 6.1 | 0.2 | 1 | 100 | excellent | 60 | 20 mM Hepes pH 6.2 |
| SPM/Chol | $K_2SO_4$ pH 6.1 | 0.2 | 0.5 | 80 | poor | 70 | 20 mM Hepes pH 7.0 |
| SPM/Chol | $K_2SO_4$ pH 6.1 | 0.2 | 0.5 | 100 | excellent | 70 | 20 mM Hepes pH 5.5 |

[a]300 mM unless otherwise indicated.
[b]Initial D/L ratio, given in (mol:mol) for ciprofloxacin
[c]Ionophore/Lipid ratio (ng nigericin/μmol lipid).

NIG/μmol lipid. Under these conditions, a ΔpH of 2.3, measured using [$^{14}$C]methylamine (see Harrigan, et al., Biophys. J. 63:1336–1345 (1992)), was present following drug uptake. This is in agreement with early data of Deamer and coworkers, who found that nigericin could form a pH gradient of 2.2 units across sonicated vesicle membranes. See, Deamer, et al., Biochim. Biophys. Acta 274:323–335 (1972).

Figure 9A:
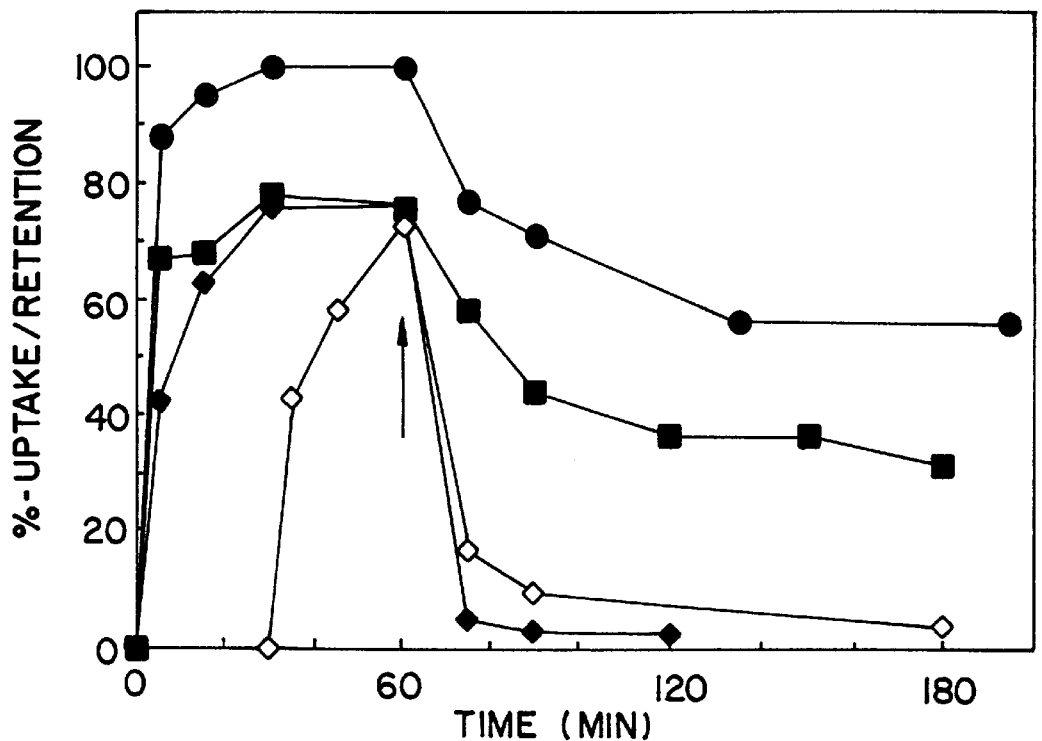
FIGS. 9A and B illustrate the uptake of ciprofloxacin (FIG. 9A) and vincristine (FIG. 9B) in 100 nm SPM/Chol LUVs at 60° C. and retention in the presence of 50% mouse serum at 37° C.
Figure 9B:
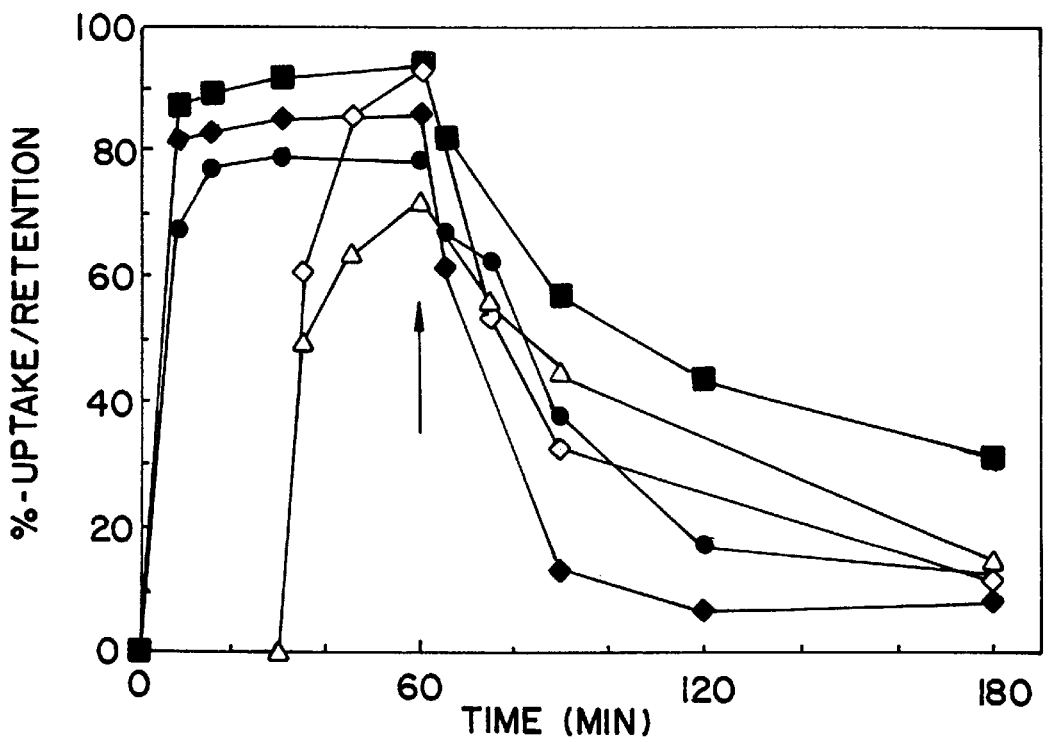
In FIG. 9B, uptake experiments were performed for the following combinations of ionophore/internal salt: A23187/$MnSO_4$ (■), nigericin/$K_2SO_4$ (♦), nigericin/$KH_2PO_4$ (●), nigericin/$K_2SO_4$ ($pH_i$=7.4, $pH_o$=6.0) (◇), and nigericin/$K_2$-tartrate ($pH_i$=7.4, $pH_o$=6.0) (△). For the latter two preparations, both the internal and external pHs ($pH_i$ and $pH_o$, respectively) were adjusted prior to uptake, and the external solution was 20 mM MES 300 mM sucrose pH 6.0. All internal salts were present at 300 mM. The arrow indicates the addition of mouse serum (to a final concentration of 50%) and transfer of the sample to 37° C.

VINC uptake in response to $K_2$-tartrate was also examined in SPM/Chol LUVs, resulting in 70% uptake (FIG. 9B and Table 2).

Figure 6A:
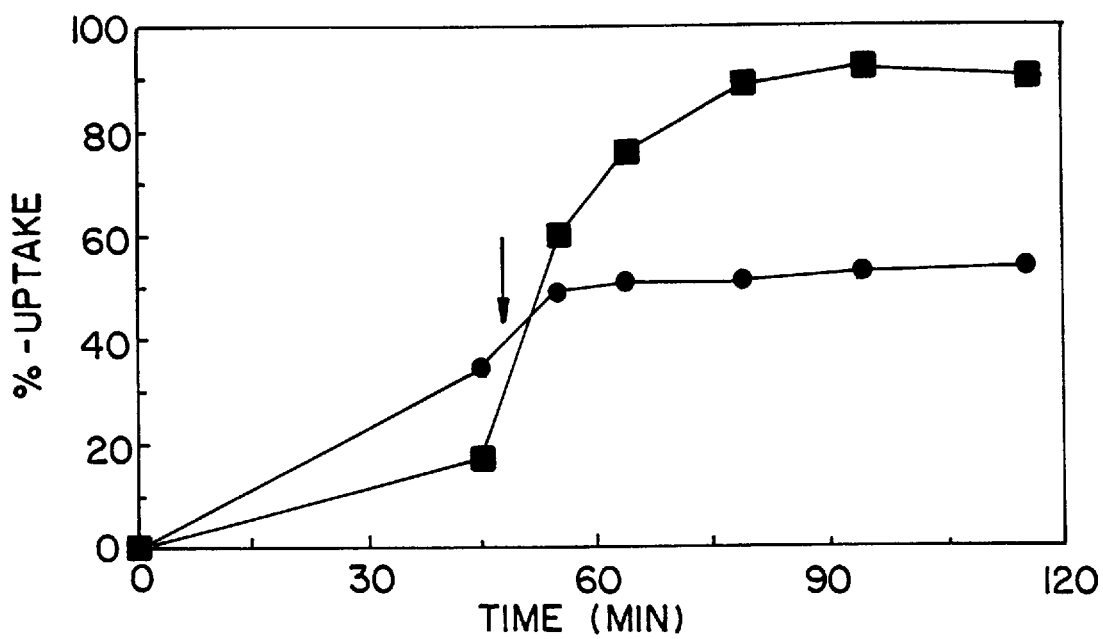
FIGS. 6A and B illustrate the effect of external EDTA on the uptake of ciprofloxacin in 100 nm DSPC/Chol LUVs (FIG. 6A) or 100 nm SPM/Chol LUVs (FIG. 6B) containing 300 mM $MnSO_4$.

It is important to note that for the $K_2$-tartrate systems the external pH was adjusted using arginine rather than NaOH, as use of the latter gave low uptake levels. Nigericin has a relatively high affinity for $Na^+$ ions and the presence of $Na^+$ ion in the external medium acts to dissipate any induced pH gradient. A summary of these results is given in Table 2.

and external EDTA are shown in FIG. 6A for uptake of CIPRO (initial D/L=0.35) into DSPC/Chol (55:45) LUVs at 60° C. Two samples were prepared with 300 mM sucrose in the external medium, with one sample also containing 3 mM EDTA. At time=0 min, the LUVs and CIPRO were combined and placed in a water bath at 60° C. Solutions of $MnSO_4$ are acidic (pH 3–4), and some uptake was expected to be observed prior to the addition of the A23187. At 45 min, about 35% uptake was observed in the sample without EDTA, and about 18% in the EDTA-containing sample. In the latter case, the EDTA lowers the external pH and therefore ΔpH, which accounts for the lower uptake (the uptake is also pH dependent, as discussed below). These values are probably close to the maximum uptake observed without ionophore, as a second trial involving a 5 min incubation exhibited similar uptakes. At t=47 min, A23187 was added to give a final concentration of 0.1 μg/μmol lipid (arrow). In the absence of external EDTA, a further small uptake to about 55% occurred, which was stable over a

TABLE 2

Summary of Vincristine Loading Using Nigericin/$K^+$ Systems

| Lipid Composition | Internal Salt[a] | D/$L_i$[b] | I/L[c] | %-uptake | Retention | T (°C.) | external solution: 300 mM sucrose + |
|---|---|---|---|---|---|---|---|
| (B) Vincristine | | | | | | | |
| DSPC/Chol | $K_2$-tartrate pH 7.4 | 0.05 | 1 | 85–90 | excellent | 60 | 20 mM HEPES pH 5.3–6.3 |
| SPM/Chol | $K_2SO_4$ pH 7.4 | 0.05 | 1 | 92 | n.d.[d] | 60 | 20 mM HEPES or MES pH 6.0 |
| SPM/Chol | $K_2$-tartrate pH 7.4 | 0.05 | 1 | 70 | n.d.[d] | 60 | 20 mM MES pH 6.0 |
| SPM/Chol | $KH_2PO_4$ | 0.05 | 1 | 80 | excellent | 60 | |
| SPM/Chol | $K_2HPO_4$ | 0.05 | 1 | <5 | n.d.[d] | 60 | |

[a]300 mM unless otherwise indicated.
[b]Initial D/L ratio, given in (wt:wt) for vincristine.
[c]Ionophore/Lipid ratio (ng nigericin/μmol lipid).
[d]not determined.

EXAMPLE 3

This example illustrates the ionophore-mediated uptake of CIPRO into liposomes having an encapsulated divalent metal ion.

The carboxylic ionophore A23187 transports divalent cations across membranes with specificity $Mn^{2+}$>$Ca^{2+}$>$Mg^{2+}$ and relative binding affinities of 210:2.6:1, respectively. See, Pressman, Ann. Rev. Biochem. 45:501–530 (1976). Few salts of $Ca^{2+}$ are soluble in aqueous solution, and the major exception ($CaCl_2$) suffers from the high membrane solubility of HCl, which contributes to the loss of any induced pH gradient. As protons are pumped into the vesicle interior, HCl is formed which diffuses out of the vesicle, thereby reducing or collapsing the pH gradient. One solution involves the use of salts with membrane impermeable anions, such as sulfate. In the present case, some CIPRO uptake (40%) was observed using 100 nm DSPC/Chol LUVs containing 300 mM $CaCl_2$, but significant leakage of the drug began within 30 minutes of uptake (Table 3). Although improvements may be observed if an external chelator is used (as discussed below), the presence of $Cl^-$ would still compromise the gradient and lead to drug loss. Salts of $Mn^{2+}$ and $Mg^{2+}$ were also examined with particular attention to $Mn^{2+}$ in light of its significantly higher relative binding affinity for A23187.

FIG. 6 details the uptake of CIPRO in response to gradients of 300 mM $MnSO_4$. The effect of both ionophore period of 3 hours. In the presence of external EDTA, further uptake of CIPRO, to a final level of >90%, occurred over a period of 45 min. This was increased to 95% by reducing the initial D/L to 0.27 (Table 3). Thus even when beginning with an acidic internal salt solution, the ionophore is necessary to obtain acceptable uptake values. Furthermore, the presence of an external chelator such as EDTA is essential to maximize uptake. This may be necessary to prevent $Mn^{2+}$: $Mn^{2+}$ "cycling," wherein back-transport of external $Mn^{2+}$ in close contact with the membrane surface is favored over the transport of protons. The necessity for external EDTA is also consistent with the observation that <½ of entrapped $Mn^{2+}$ is released from POPC vesicles in the presence of A23187, even though a large $Mn^{2+}$ gradient is still present (see, Erdahl, et al., Biophys. J. 66:1678–1693 (1994)).

Figure 6B:
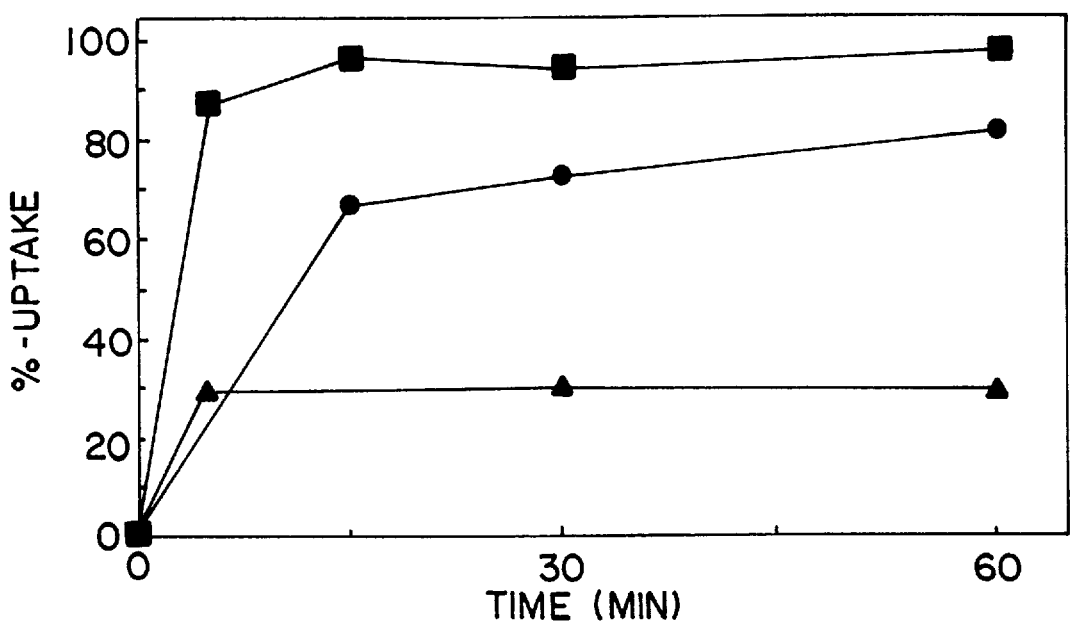
In FIG. 6B, the external medium was 300 mM sucrose 15 mM EDTA pH 5.9 (■), 300 mM sucrose 15 mM EDTA pH 4.4 (●), or 300 mM sucrose (▲). The A23187 (0.1 $\mu$g/$\mu$mol lipid) was added at time 0. The uptake temperature was 60° C., and the initial D/L ratio was 0.2 (mol:mol).

The uptake of CIPRO into LUVs composed of SPM/Chol (55:45) is shown in FIG. 6B. For these experiments, the D/L ratio was reduced to 0.2, and the external EDTA was increased to 15 mM. As above, low uptake (30%) was observed in the absence of EDTA. However, even in the presence of EDTA, the final entrapment levels were dependent on the external pH. Only 80% uptake was observed at $pH_{outside}$=4.4, but this was increased to 98–100% at $pH_{outside}$=5.9. The pH optimum for the uptake of CIPRO, via both nigericin and A23187, therefore appears to be around pH 6.

Figure 7:
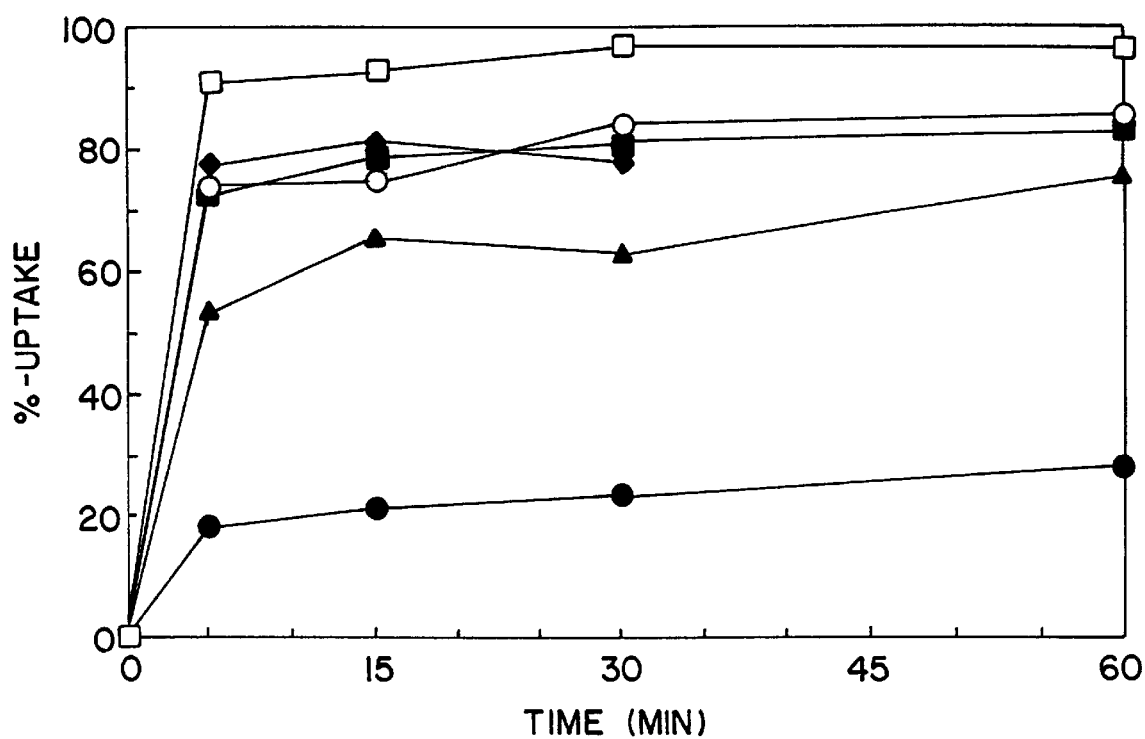
FIG. 7 illustrates the effect of external pH and ionophore concentration on the uptake of ciprofloxacin in 100 nm SPM/Chol LUVs containing 300 mM $MgSO_4$ pH 6.5. For 0.1 $\mu$g A23187/$\mu$mol lipid, the external medium was 20 mM HEPES 300 mM sucrose 15 mM EDTA pH 7.0 (■), 300 mM sucrose 15 mM EDTA pH 7.0 (♦), 300 mM sucrose 15 mM EDTA pH 5.9 (▲), 300 mM sucrose 15 mM EDTA pH 4.4 (●), or 20 mM HEPES 300 mM sucrose 15 mM EDTA pH 6.0 (○). For 0.5 $\mu$g A23187/$\mu$mol lipid, the external medium was 20 mM HEPES 300 mM sucrose 15 mM EDTA pH 6.0 (□).

Reasonable to excellent encapsulation of CIPRO also occurs in response to gradients of $MgSO_4$ as shown in FIG. 7. The internal salt was 300 mM $MgSO_4$ (pH 6.5), and the external medium was 300 mM sucrose containing 15 mM EDTA. The lipid composition, uptake temperature, and A23187 concentration were as for FIG. 6B. Only 20% uptake was observed for $pH_{outside}$=4.4, approximately 75% at $pH_{outside}$=5.9 (sucrose-EDTA), and 86% at $pH_{outside}$=6.0 (20 mM HEPES+sucrose-EDTA). The better uptake observed at pH 6.0 as compared to pH 5.9 stems from the presence of the HEPES buffer. For $pH_{outside}$=7.0 uptake levels of 80% were observed. However, increasing the A23187 concentration 5-fold (to 0.5 μg/μmol lipid) for an external pH of 6.0 results in 97% entrapment. A summary of these results is given in Table 3.

TABLE 3

Summary of Ciprofloxacin Loading Using A23187 Systems

| Lipid Composition | Internal Salt[a] | $D/L_i$[b] | $I/L$[c] | %-uptake | Retention | T (°C.) | external solution: 300 mM sucrose + |
|---|---|---|---|---|---|---|---|
| (A) Ciprofloxacin | | | | | | | |
| DSPC/Chol | $CaCl_2$ | 0.3 | 1.0 | 40 | poor | 60 | |
| DSPC/Chol | $CaCl_2$ | 0.3 | 0.1 | 40 | poor | 60 | |
| DSPC/Chol | $MnSO_4$ | 0.27–0.35 | 0.1 | 40–50 | excellent | 60 | |
| DSPC/Chol | $MnSO_4$ | 0.27–0.35 | 0.1 | 95 | excellent | 60 | 3 mM EDTA |
| DSPC/Chol | $MgSO_4$ | 0.34 | 1.0 | 20 | excellent | 60 | |
| SPM/Chol | $MnSO_4$ | 0.2 | 0.1 | 70–80 | excellent | 60 | 15 mM BDTA pH 4.4 |
| SPM/Chol | $MnSO_4$ | 0.2 | 0.1 | 98 | excellent | 60 | 15 mM EDTA pH 59 |
| SPM/Chol | $MgSO_4$ pH 6.5 | 0.2 | 0.1 | 25 | excellent | 60 | 15 mM EDTA pH 4.4 |
| SPM/Chol | $MgSO_4$ pH 6.5 | 0.2 | 0.1 | 75 | excellent | 60 | 15 mM EDTA pH 5.9 |
| SPM/Chol | $MgSO_4$ pH 6.5 | 0.2 | 0.1 | 80 | excellent | 60 | 15 mM EDTA pH 7.0 |
| SPM/Chol | $MgSO_4$ pH 6.5 | 0.2 | 0.1 | 80 | excellent | 60 | 20 mM Hepes 15 mM EDTA pH 7.0 |
| SPM/Chol | $MgSO_4$ pH 6.5 | 0.2 | 0.1 | 86 | excellent | 60 | 20 mM Hepes 15 mM EDTA pH 6.0 |
| SPM/Chol | $MgSO_4$ pH 6.5 | 0.2 | 0.5 | 97 | excellent | 60 | 20 mM Hepes 15 mM EDTA pH 6.0 |

[a] 300 mM unless otherwise indicated.
[b] Initial D/L ratio.
[c] Ionophore/Lipid ratio (μg A23187/μmol lipid).

EXAMPLE 4

This example describes ionophore-mediated uptake of VINC into liposomes containing $Mn^{2+}$.

Figure 8:
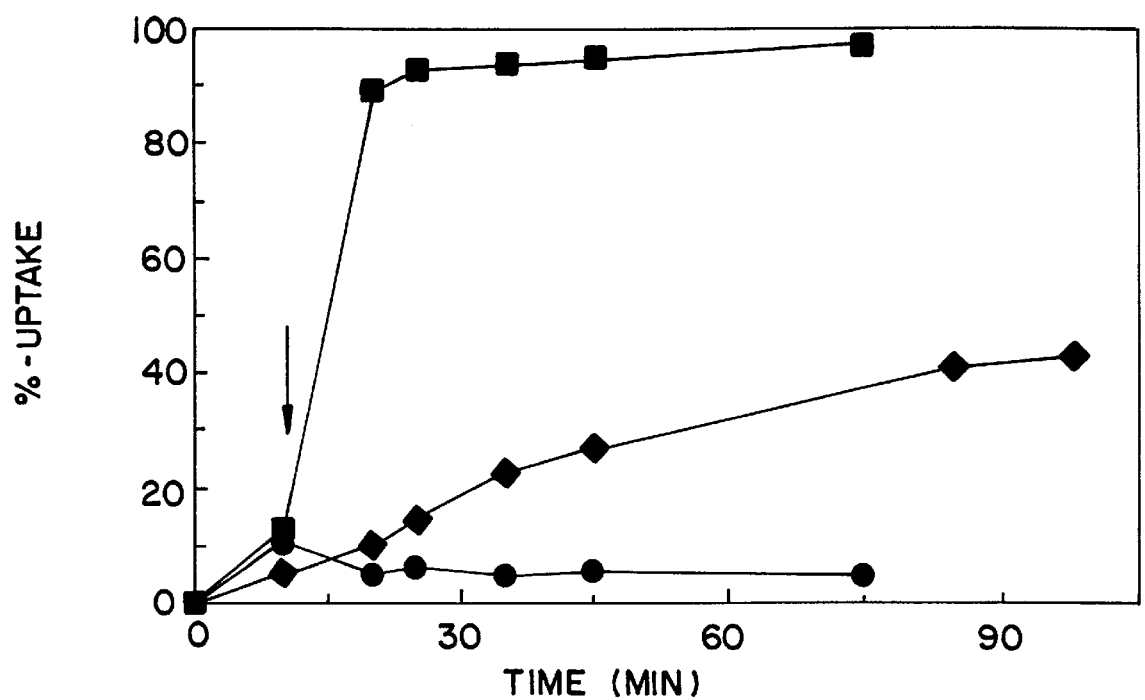
FIG. 8 illustrates the effect of external pH and EDTA on the uptake of vincristine in 100 nm SPM/Chol LUVs containing 300 mM $MnSO_4$. The external medium was 20 mM HEPES 300 mM sucrose 3 mM EDTA pH 7.5 (■), 300 mM sucrose 3 mM EDTA (♦), or 20 mM HEPES 300 mM sucrose pH 7.5 (●). The addition of A23187 (0.1 $\mu$g/$\mu$mol lipid) is indicated by the arrow. The uptake temperature was 60° C., and the initial D/L ratio was 0.05 (wt:wt).

Excellent uptake and retention of VINC can also be obtained using $Mn^{2+}$/A23187 with SPM/Chol LUVs (see FIG. 8). Less than 5% uptake was observed when there was no EDTA present in the external medium of Hepes-buffered sucrose (pH 7.5). In the presence of 3 mM EDTA ($pH_{outside}$= 7.5), over 95% uptake was observed within one hour. However, extremely poor uptake (40%) is observed at lower external pHs when using 300 mM sucrose 3 mM EDTA. A summary of these results is given in Table 4.

TABLE 4

Summary of Vincristine Loading Using A23187 Systems

| Lipid Composition | Internal Salt[a] | $D/L_i$[b] | $I/L$[c] | %-uptake | Retention | T (°C.) | external solution: 300 mM sucrose + |
|---|---|---|---|---|---|---|---|
| (B) Vincristine | | | | | | | |
| SPM/Chol | $MnSO_4$ | 0.05 | 0.1 | 5 | n.a. | 60 | |
| SPM/Chol | $MnSO_4$ | 0.05 | 0.1 | 40 | excellent | 60 | 3 mM EDTA |

TABLE 4-continued

Summary of Vincristine Loading Using A23187 Systems

| Lipid Composition | Internal Salt[a] | $D/L_i$[b] | $I/L$[c] | %-uptake | Retention | T (°C.) | external solution: 300 mM sucrose + |
|---|---|---|---|---|---|---|---|
| SPM/Chol | MnSO$_4$ | 0.05 | 0.1 | >95 | excellent | 60 | 20 mM HEPES 3 mM EDTA pH 7.5 |

[a]300 mM unless otherwise indicated.
[b]Initial D/L ratio.
[c]Ionophore/Lipid ratio (μg A23187/μmol lipid).

EXAMPLE 5

This example illustrates the stability of the present liposome compositions to mouse serum.

Release of CIPRO and VINC from LUVs in response to mouse serum

An in vitro leakage assay has been designed which employs mouse serum to assess the relative retentive properties of the various liposomal systems. The assay is extremely simple, involving the incubation of equal volumes of mouse serum and LUV (loaded with drug) at 37° C., followed by the application of aliquots to spin columns to quantitate the change in D/L ratio with time. This quantity of serum is sufficient to induce rapid, almost complete leakage of certain drugs. However, leakage in vivo generally occurs at a much slower rate. The results obtained using this assay differ from other methods involving dialysis, but the relative differences observed between different samples have been found to be similar regardless of the method used. The simple assay is therefore a useful tool for screening preparations prior to in vivo testing.

The release of CIPRO from SPM/Chol LUVs resulting from incubation in 50% mouse serum at 37° C. is shown in FIG. 9A. The best retention of drug was observed for the Mn$^{2+}$/A23187 system (60% remaining after 2 hours), followed by the Mg$^{2+}$/A23187 system (35%) and finally by the K$^+$/nigericin system. The much more rapid loss of material from LUVs containing nigericin may result from high serum concentrations of K$^+$, which would cause reverse transport and reduce or collapse the pH gradient.

The release of VINC from SPM/Chol LUVs resulting from incubation in 50% mouse serum at 37° C. is shown in FIG. 9B. As with CIPRO, better retention of drug was observed for the Mn$^{2+}$/A23187 system than for the K$^+$/nigericin system. In the latter case, better retention was observed using phosphate or tartrate salts, or using sulfate salts with an external pH of 6. The retention observed with the Mn$^{2+}$/A23187 system was similar to that observed for LUVs loaded using methylammonium sulfate (results not shown).

EXAMPLE 6

This example illustrates methods for the removal of ionophores from loaded liposomes.

Following drug uptake and in vivo administration, the presence of ionophores in LUVs can be disadvantageous for two reasons. First, high serum concentrations of ions such as Na$^+$ and K$^+$ may cause reverse transport with loss of the induced pH gradient. Second, some ionophores are considered toxic compounds. Consequently, methods for reducing their concentration would be of value pharmacologically. Using a fluorimetric assay, determination of A23187 concentrations in formulations of SPM/Chol can be quantified before and after various treatments (this data will be discussed below). For nigericin, the potential for reducing nigericin concentrations utilizing spin columns and dialysis has been assessed by examining the uptake of CIPRO following various treatments of an LUV sample. These studies were prompted by the knowledge that ionophores will exchange between vesicles, and therefore can be removed from lipid bilayers. See, Erdahl, et al., *Biophys. J.* 66:1678–1693 (1994).

The effect on drug uptake of passing a vesicle bearing nigericin down a spin column prior to loading is shown in FIG. 10. If the ionophore (1 ng NIG/μmol lipid) and drug (D/L=0.2) were added at the same time following establishment of the ion gradient, 80% entrapment was observed within 30 min. However, if prior to addition of the drug, the LUV sample was passed down a G-50 spin column, the rate of uptake was significantly reduced, and the time to achieve similar uptake levels was increased by a factor of 4. The shape of the this uptake curve resembled that observed for 0.5 ng NIG/μmol lipid at 70° C., and illustrates the removal of a significant proportion of the nigericin. If the LUVs bearing nigericin were first subjected to dialysis (3 hours), or if they were passed down a second spin column, similar uptake rates were observed, suggesting little or no further removal of nigericin. Interestingly, the in vitro leakage rates of CIPRO from normal and nigericin-reduced LUVs were found to be identical (not shown).

Figure 10A:
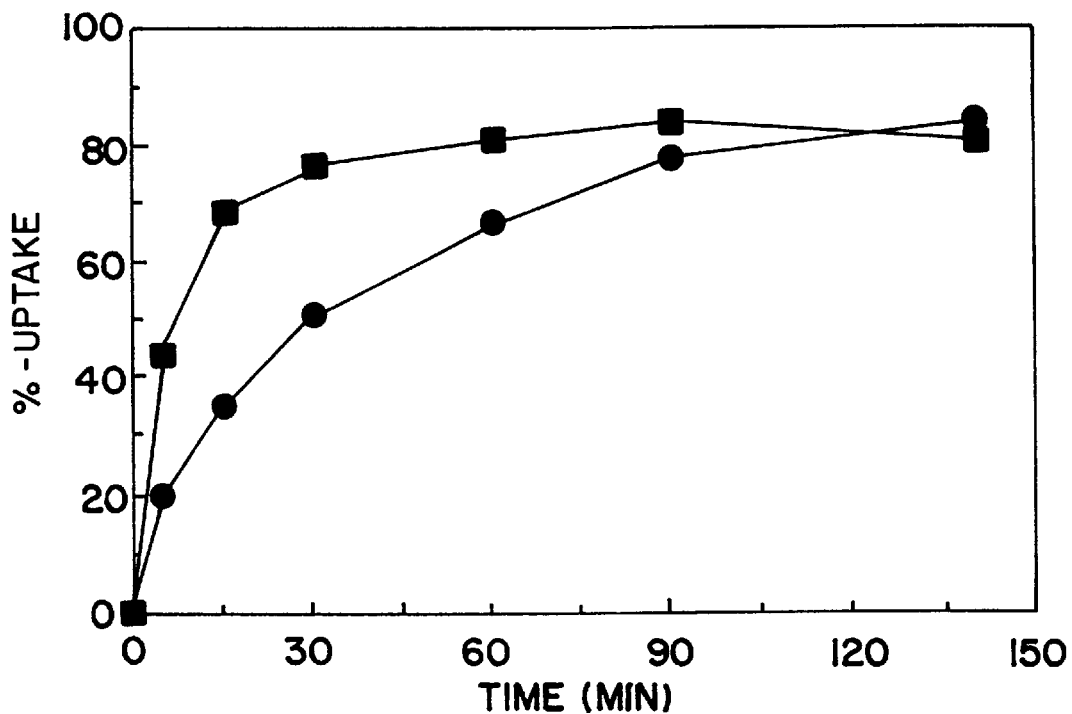
FIGS. 10A and B illustrate the removal of nigericin from SPM/Chol LUVs as assayed by drug uptake.
Figure 10B:
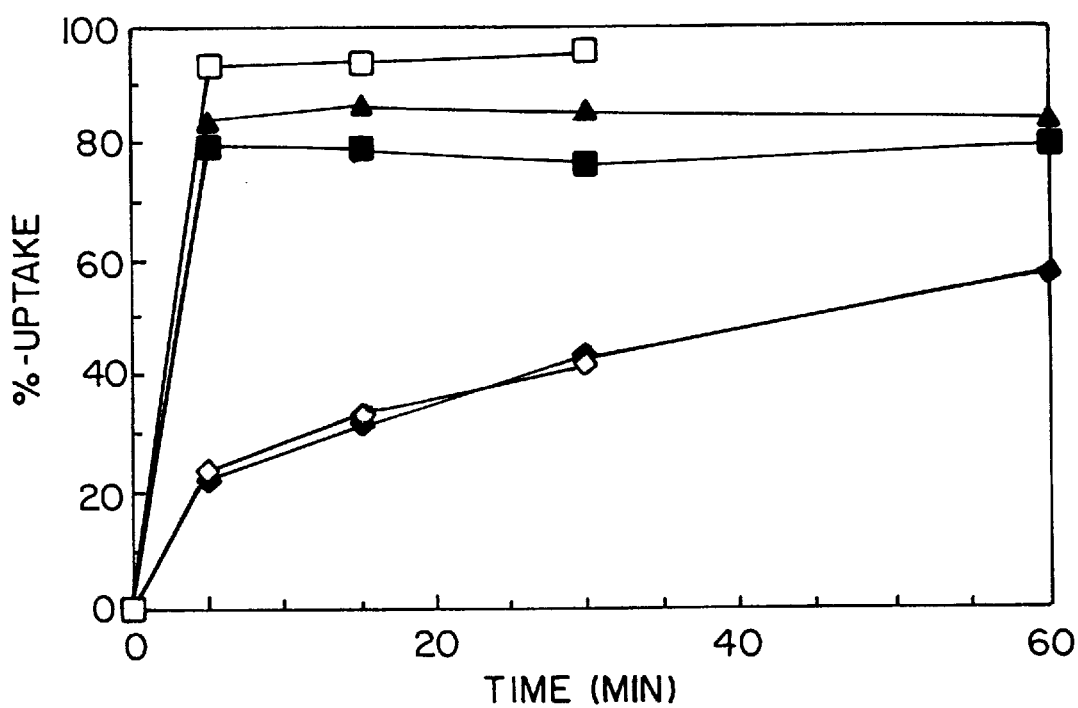
FIG. 10B illustrates the effect of dialysis on uptake of vincristine by ionophore and amine methods at 60° and 65° C.

The partial success in removing nigericin from vesicles using spin columns indicated that greater reductions in ionophore concentrations could be achieved using more extreme measures. Thus, an aliquot of nigericin (1 ng NIG/μmol lipid) was added to a sample of SPM/Chol LUVs containing 300 mm KH$_2$PO$_4$ and the temperature was increased to 60° C. for 5 min to ensure association of nigericin with the lipid. The sample was then exhaustively dialysed at room temperature against 300 mM sucrose for 20 hours, following which an aliquot was passed down a spin column prior to drug loading with VINC (FIG. 10B). Despite the extensive dialysis, the uptake of VINC at 1 hr (60%) was only slightly lower than that obtained for CIPRO using a single spin column (FIG. 10A).

Although these results are best explained in terms of loss of ionophore from the vesicles, reduced uptake would also be observed if the vesicle contents were to leak out during the course of dialysis. To ensure that such was not the case, control uptake experiments were performed on LUVs containing ethylammonium sulfate and amylammonium sulfate which were subjected to the same conditions. These amines, which cause drug uptake and retention, gave 80–95% encapsulation. Furthermore, the results were identical to samples in which the amine gradient was prepared fresh on a 1.5×10 cm G-50 column. This demonstrates that the loss of amine over the course of dialysis was negligible, and argues against any loss of $K^+$ ions, which have a lower membrane permeability. Taken together, these results strongly suggest that while nigericin can be partially removed from LUVs, complete removal may not be feasible.

As mentioned above, the concentration of A23187 in LUVs can be quantitated using a fluorimetric assay which allows determination of the amount remaining following various purification procedures. The results are given in Table 5 for SPM/Chol LUVs initially containing A23187 at a concentration of 0.1 µg/µmol lipid. For sample 1 (S1), 146 ng of A23187 was added to the LUVs, and 123 ng was measured by the assay. Following passage of the LUVs down a Sephadex G-50 column eluted with 300 mM sucrose (S2), the remaining levels were below background. Likewise, dialysis against 300 mM sucrose (S3), or treatment with SM-2 biobeads (S4) reduced the A23187 concentration below background levels. The addition of known aliquots of ionophore to S4 resulted in expected concentrations in the LUVs. The results demonstrate that A23187 can be effectively removed from LUVs, in contrast to the incomplete removal observed with nigericin. These results have significance for the in vivo studies reported below.

TABLE 5

Fluorimetric determination of A23187 in a liposomal formulation.

| Sample No. | A23187 removal method | Initial amount of A23187 (ng) | Amount of A23187 measured (ng) |
|---|---|---|---|
| S1 | none | 146 | 123 |
| S2 | Sephadex G-50 column | 109 | n.d.[a] |
| S3 | Dialysis (1 br) | 500 | n.d.[a] |
| S4 | SM-2 biobeads | 500 | n.d.[a] |
| S4 + 45 ng A23187 | none | 45 | 41 |
| S4 + 90 ng A23187 | none | 90 | 94 |

[a]not determined (number is either at background level or is <15 ng).

EXAMPLE 7

Figure 11A:
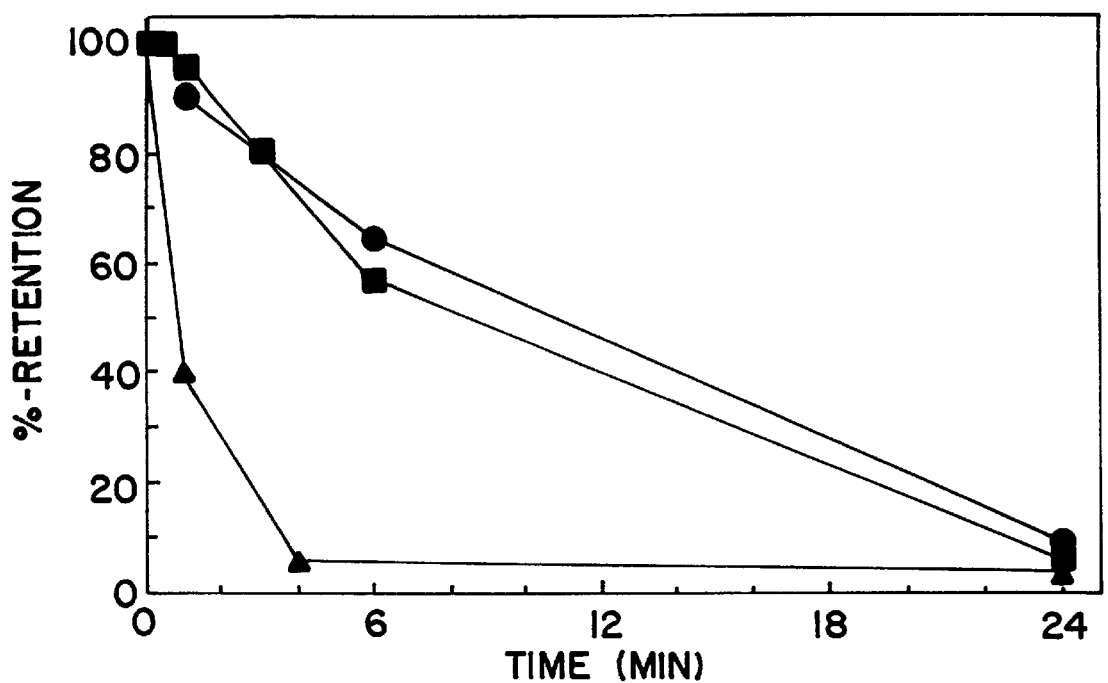
FIGS. 11A and B illustrate the in vivo retention of ciprofloxacin (FIG. 11A) and vincristine (FIG. 11B) in 100 nm SPM/Chol (55/45 mol %) LUVs. Drug to lipid ratios were determined following i.v. administration in mice of liposomal ciprofloxacin (A) containing 300 mM methylammonium sulfate (●), 300 mM $MnSO_4$/A23187 (■), or 300 mM $K_2SO_4$/nigericin (▲), or of liposomal vincristine (B) containing 300 mM citrate pH 4.0 (●) or 300 mM $MnSO_4$/A23187 (■). Ciprofloxacin was encapsulated at a D/L ratio of 0.2 (mol:mol), and was measured using [$^{14}$C]CIPRO as a tracer. Vincristine was encapsulated at a D/L ratio of 0.05 (wt:wt), and was measured using [$^3$H]vincristine as a tracer. Lipid was measured using [$^{14}$C]cholesteryl hexadecyl ether as a tracer. The %-retention is defined as the D/L ratio at time t divided by the initial measured drug to lipid ratio.
Figure 11B:
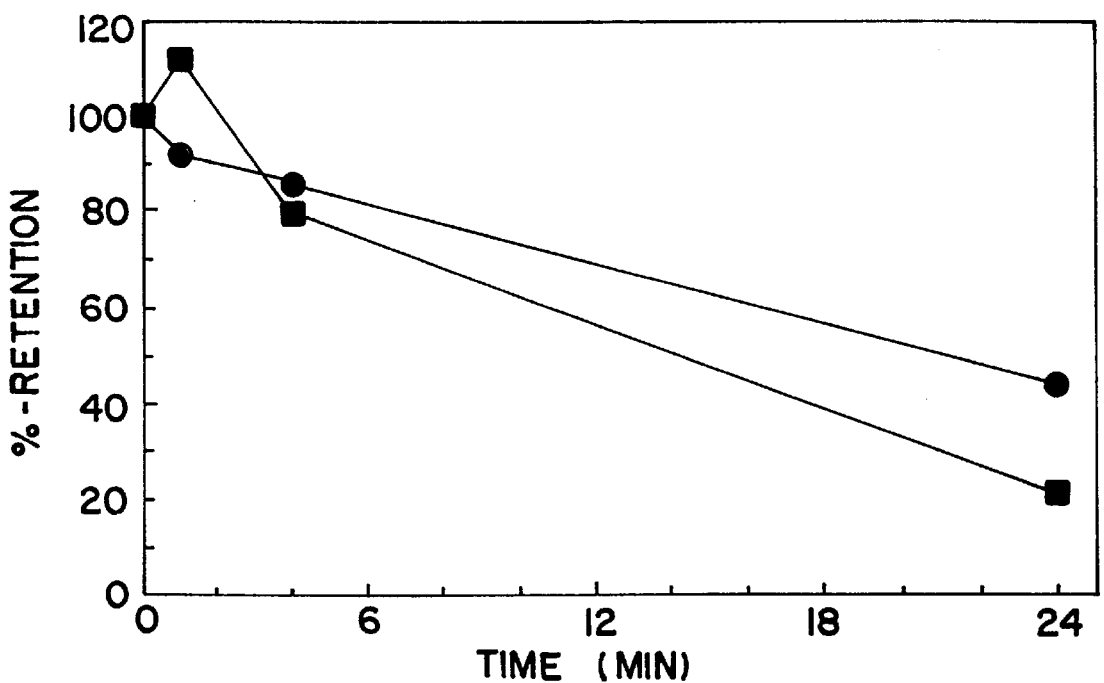

In Vivo Pharmacokinetics of Liposomal CIPRO and VINC. The pharmacokinetics of CIPRO and VINC loaded into SPM/Chol LUVs are shown in FIG. 11. Each drug was loaded using several methods, and was injected at time 0 into mice. At the indicated times, samples were withdrawn and the D/L ratio of the recovered LUVs was determined. For CIPRO (FIG. 11A), the A23187 system was superior to $K_2SO_4$/Nigericin, and was similar to LUVs containing methylammonium sulfate. The half-lives for release of CIPRO from the LUVs were 6.8 hours, 5.6 hours, and 1.1 hours for methylammonium sulfate, A23187, and nigericin, respectively. If one examines the half-lives of CIPRO in circulation, the values were 3.5 hours, 3.1 hours, and 0.7 hours, respectively. For VINC (FIG. 11B), the retention observed for LUVs loaded using A23187 was comparable to LUVs loaded using 300 mM citrate pH 4.0. In this case, the half-lives for release of VINC from the LUVs (based on changes in the initial D/L ratio) were 20.9 hours and 10.1 hours for citrate and A23187, respectively, and the half-lives of VINC in circulation were 8.5 hours and 6.0 hours, respectively. Although the drug leakage half-lives differ by a factor of two, the differences in VINC circulation half-lives are not as great. This suggests that the efficacy achievable with the two systems may be comparable.

VII. Conclusion

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of loading a weakly basic drug into liposomes comprising incubating said liposomes having an encapsulated medium comprising a salt of a divalent metal ion with an external solution comprising said weakly basic drug and an ionophore to form drug-loaded liposomes.

2. A method in accordance with claim 1, wherein said external solution further comprises a chelating agent.

3. A method in accordance with claim 1, further comprising terminating said incubation by removing unloaded drug and ionophore and isolating said drug-loaded liposomes.

4. A method in accordance with claim 1, wherein said divalent metal ion is a member selected from the group consisting of $Mn^{++}$, $Mg^{++}$, $Ca^{++}$, $Fe^{++}$ and $Ba^{++}$.

5. A method in accordance with claim 1, wherein said ionophore is a member selected from the group consisting of A23187, X-537A, ionomycin and 4Br-A23187.

6. A method in accordance with claim 1, wherein said ionophore is present in an amount of from about 10 ng to about 2000 ng per µmol of lipid.

7. A method in accordance with claim 1, wherein said ionophore is present in an amount of from about 100 ng to about 500 ng per µmol of lipid.

8. A method in accordance with claim 1, wherein said chelating agent is present in said external solution in a concentration of from about 1 mM to about 50 mM.

9. A method in accordance with claim 2, wherein said chelating agent is present and is a member selected from the group consisting of ethylene diamine tetraacetic acid, ethylene glycol-bis(β-aminoethyl ether) N,N,N',N'-tetraacetic acid and 2-[(2-bis[carboxymethyl]amino-5-methylphenoxy) methyl]-6-methoxy-8-bis-carboxymethyl aminoquinoline.

10. A method in accordance with claim 1, wherein said weakly basic drug is a member selected from the group consisting of mitoxantrone, epirubicin, daunorubicin, doxorubicin, vincristine, vinblastine, lidocaine, chlorpromazine, ciprofloxacin, dibucaine, propranolol, timolol, quinidine, pilocarpine, physostigmine, dopamine, serotonin, imipramine, diphenhydramine, quinine, chloroquine, quinacrine and codeine.

11. A method in accordance with claim 1, wherein said weakly basic drug is a member selected from the group consisting of ciprofloxacin, doxorubicin, vincristine and epirubicin.

12. A method in accordance with claim 1, wherein said external solution has a pH of about 5.0–6.5, said drug is ciprofloxacin, said divalent metal ion is $Mn^{++}$, said ionophore is A23187, said liposomes comprise a lipid bilayer consisting essentially of sphingomyelin and cholesterol, and said chelator is present and is ethylene diamine tetraacetic acid.

13. A method in accordance with claim 1, wherein said external solution has a pH of about 6.0–7.5, said drug is vincristine, said divalent metal ion is $Mn^{++}$, said ionophore is A23187, said liposomes comprise a lipid bilayer consisting essentially of sphingomyelin and cholesterol, and said chelator is present and is ethylene diamine tetraacetic acid.

14. A method in accordance with claim 2, wherein said isolating further comprises removing said ionophore from said drug-loaded liposomes.

15. A method of loading a weakly basic drug into liposomes comprising incubating said liposomes having an encapsulated medium comprising a salt of a monovalent metal ion with an external solution comprising said weakly basic drug and an ionophore to form drug loaded liposomes, wherein said ionophore facilitates the electroneutral transport of a metal ion out of the liposome in exchange for inward movement of hydrogen ions and is present in said external medium in an amount of from about 0.1 ng to about 2000 ng per μmol of lipid.

16. A method in accordance with claim 15, wherein said ionophore is initially present in said external medium in an amount of from about 0.1 ng to about 100 ng per μmol of lipid.

17. A method in accordance with claim 15, wherein said ionophore is initially present is said external medium in an amount of from about 0.5 ng to about 5.0 ng per μmol of lipid.

18. A method in accordance with claim 15, further comprising terminating said incubation by removing unloaded drug and ionophore and isolating said drug-loaded liposomes.

19. A method in accordance with claim 15, wherein said monovalent metal ion is a member selected from the group consisting of $K^+$ and $Na^+$.

20. A method in accordance with claim 15, wherein said ionophore is a member selected from the group consisting of nigericin, monensin and dianemycin.

21. A method in accordance with claim 15, wherein said weakly basic drug is a member selected from the group consisting of mitoxantrone, epirubicin, daunorubicin, doxorubicin, vincristine, vinblastine, lidocaine, chlorpromazine, ciprofloxacin, dibucaine, propranolol, timolol, quinidine, pilocarpine, physostigmine, dopamine, serotonin, imipramine, diphenhydramine, quinine, chloroquine, quinacrine and codeine.

22. A method in accordance with claim 15, wherein said weakly basic drug is a member selected from the group consisting of ciprofloxacin, doxorubicin, vincristine and epirubicin.

23. A method in accordance with claim 15, wherein said external solution has a pH of about 5.0–6.5, said drug is ciprofloxacin, said monovalent metal ion is $K^+$, said ionophore is nigericin, and said liposomes comprise a lipid bilayer consisting essentially of sphingomyelin and cholesterol.

24. A method in accordance with claim 15, wherein said external solution has a pH of about 5.0–6.5, said drug is vincristine, said monovalent metal ion is $K^+$, said ionophore is nigericin, and said liposomes comprise a lipid bilayer consisting essentially of sphingomyelin and cholesterol.

25. A method in accordance with claim 16, wherein said isolating further comprises removing said ionophore from said drug-loaded liposomes by gel exclusion chromatography.

* * * * *